United States Patent
Fukudome

(10) Patent No.: US 11,325,993 B2
(45) Date of Patent: May 10, 2022

(54) CHEMICAL POLYMERIZATION INITIATOR, ADHESIVE COMPOSITION, ADHESIVE COMPOSITION KIT, DENTAL MATERIAL, DENTAL MATERIAL KIT, AND METHOD OF STORING ADHESIVE COMPOSITION

(71) Applicant: TOKUYAMA DENTAL CORPORATION, Tokyo (JP)

(72) Inventor: Keishi Fukudome, Tokyo (JP)

(73) Assignee: TOKUYAMA DENTAL CORPORATION

( * ) Notice: Subject to any disclaimer, the term of this patent is extended or adjusted under 35 U.S.C. 154(b) by 266 days.

(21) Appl. No.: 16/756,695

(22) PCT Filed: Dec. 10, 2018

(86) PCT No.: PCT/JP2018/045345
§ 371 (c)(1),
(2) Date: Apr. 16, 2020

(87) PCT Pub. No.: WO2019/131094
PCT Pub. Date: Jul. 4, 2019

(65) Prior Publication Data
US 2020/0239604 A1    Jul. 30, 2020

(30) Foreign Application Priority Data

Dec. 26, 2017 (JP) .............................. JP2017-249143
Apr. 5, 2018 (JP) .............................. JP2018-073435

(51) Int. Cl.
| | | |
|---|---|---|
| *C08F 4/40* | (2006.01) | |
| *A61K 6/887* | (2020.01) | |
| *A61K 6/61* | (2020.01) | |
| *C09J 4/00* | (2006.01) | |
| *C09J 11/06* | (2006.01) | |

(52) U.S. Cl.
CPC ............... *C08F 4/40* (2013.01); *A61K 6/61* (2020.01); *A61K 6/887* (2020.01); *C09J 4/00* (2013.01); *C09J 11/06* (2013.01); *C09J 2400/10* (2013.01); *C09J 2433/00* (2013.01)

(58) Field of Classification Search
CPC ...................................................... A61K 6/61
See application file for complete search history.

(56) References Cited

U.S. PATENT DOCUMENTS

| 4,429,092 | A | 1/1984 | Sterling |
| 9,132,069 | B2 | 9/2015 | Hecht et al. |
| 2002/0132951 | A1 | 9/2002 | Ibaragi et al. |
| 2002/0176826 | A1 | 11/2002 | Klee et al. |
| 2004/0006154 | A1* | 1/2004 | Ibaragi ..................... A61K 6/30 523/120 |
| 2007/0040151 | A1 | 2/2007 | Utterodt et al. |
| 2007/0100019 | A1* | 5/2007 | Sun .......................... A61K 6/30 523/116 |
| 2014/0329205 | A1 | 11/2014 | Hecht et al. |
| 2016/0038382 | A1 | 2/2016 | Kawashima et al. |
| 2018/0360696 | A1 | 12/2018 | Nojiri et al. |

FOREIGN PATENT DOCUMENTS

| CN | 103865405 | A | 6/2014 |
| GB | 2075035 | A | 11/1981 |
| JP | S56-169609 | A | 12/1981 |
| JP | H11-343304 | A | 12/1999 |
| JP | 2002-187907 | A | 7/2002 |
| JP | 2007-056020 | A | 3/2007 |
| JP | 2014-152106 | A | 8/2014 |
| JP | 2014-227370 | A | 12/2014 |
| JP | 2017-088637 | A | 5/2017 |
| RU | 2600814 | C2 | 10/2016 |
| WO | 2016-007453 | A1 | 1/2016 |
| WO | 2017-098724 | A1 | 6/2017 |

OTHER PUBLICATIONS

First Chinese Office Action for corresponding Application No. 201880068082.X dated Feb. 8, 2022 with English translation (9 Pages).

* cited by examiner

*Primary Examiner* — Michael F Pepitone
(74) *Attorney, Agent, or Firm* — Harness, Dickey & Pierce, P.L.C.

(57) ABSTRACT

Provided are a chemical polymerization initiator including (a) a thiourea compound, (b) a peroxyester, (c) a divalent copper compound, and (d) an aryl borate compound, an adhesive composition, an adhesive composition kit, a dental material, and a dental material kit each using the chemical polymerization initiator, and a method of storing the adhesive composition.

14 Claims, No Drawings

CHEMICAL POLYMERIZATION INITIATOR, ADHESIVE COMPOSITION, ADHESIVE COMPOSITION KIT, DENTAL MATERIAL, DENTAL MATERIAL KIT, AND METHOD OF STORING ADHESIVE COMPOSITION

CROSS-REFERENCE TO RELATED APPLICATIONS

This application is a U.S. National Phase Application under 35 U.S.C. 371 of International Application No. PCT/JP2018/045345, filed on Dec. 10, 2018 and published in Japanese as WO 2019/131094 A1 on Jul. 4, 2019, which is based on and claims the benefit of priority from Japanese Patent Application No. 2018-073435, filed on Apr. 5, 2018 and Japanese Patent Application No. 2017-249143, filed on Dec. 26, 2017. The entire disclosures of all of the above applications are incorporated herein by reference.

BACKGROUND

Technical Field

The present invention relates to a chemical polymerization initiator, an adhesive composition, an adhesive composition kit, a dental material, a dental material kit, and a method of storing an adhesive composition.

Related Art

A material based on a (meth)acrylate has been used in a wide variety of fields, such as a paint, a printing material, an adhesive material, and a dental material. In, for example, the field of dentistry, the material has been applied to various materials, such as a bonding material, a resin cement, a resin-reinforced glass ionomer, and a composite resin. Those materials are typically cured by radical polymerization. The generation of a radical is performed by one or a plurality of kinds of polymerization initiators suitable for an application, the initiators being selected from a photopolymerization initiator, a thermal polymerization initiator, and a chemical (redox) polymerization initiator.

Of those polymerization initiators, the chemical polymerization initiator is particularly useful when the stimulus of light or heat cannot be applied. The chemical polymerization initiator is typically stored by being divided into two or more portions because the initiator contains a combination of a reducing agent and an oxidizing agent that may immediately react with each other when brought into contact with each other. Forms to be stored are a combination of a paste and another paste, a liquid and another liquid, or powder and a liquid, and after the mixture of these materials, the reducing agent and the oxidizing agent react with each other to generate a radical.

A chemical polymerization initiator that has been known since olden times is, for example, a chemical polymerization initiator obtained by combining benzoyl peroxide and a tertiary aromatic amine compound. However, benzoyl peroxide has low thermal stability, and hence has poor storage stability. In addition, the tertiary aromatic amine compound is deactivated in the presence of an acid, and hence sufficient polymerization activity is not obtained.

In the field of dentistry, many materials require acids because of, for example, the impartment of adhesive properties. Accordingly, a chemical polymerization initiator showing high polymerization activity in the presence of an acid has been required. Known examples of the chemical polymerization initiator showing high polymerization activity in the presence of an acid include initiators formed of combinations of: oxidizing agents formed of organic peroxides each having high thermal stability, such as hydroperoxides, ketone peroxides, peroxyesters, and diacyl peroxides; and reducing agents formed of amines, sulfinic acid compounds, thiourea compounds, oxime compounds, transition metal compounds, and the like (one of these materials may function as a reducing agent alone, or a plurality thereof may function as a reducing agent in combination, and hence the materials are sometimes collectively referred to as "polymerization accelerators") (see JP 2017-088637 A and WO 2017/098724 A1).

Of those, a chemical polymerization initiator obtained by combining a hydroperoxide and a thiourea compound has been suitably used particularly as a chemical polymerization initiator for dentistry because the initiator has high storage stability, and shows high activity in the presence of an acid. Various features can be imparted to the initiator by, for example, selecting a specific compound as the thiourea compound or combining the thiourea compound with a polymerization accelerator except the thiourea compound, such as a copper compound.

In, for example, JP 2007-056020 A, there is a disclosure of a two-component initiator system including: (a) a hydroperoxide compound having one or a plurality of hydroperoxide groups bonded to tertiary carbon; (b) a thiourea derivative; and (c) an accelerator for curing a polymerizable material, the accelerator having a copper compound that is soluble in a preparation, as an accelerator. In addition, in JP 2007-056020 A, there is a disclosure that a dental composition including a radical-polymerizable monomer free of an acidic group (hereinafter sometimes referred to as "nonacidic monomer") and the two-component initiator system has high storage stability in the absence of an acid component and has a short inhibition time (its polymerization immediately starts when the two-component initiator system is mixed with the monomer), and its activity is improved by the addition of an acid.

In addition, in JP 2014-227370 A, there is a disclosure of a chemical polymerization initiator containing a hydroperoxide compound (a2) and a substituted pyridylthiourea compound (a3) represented by a specific structural formula, and as required, a vanadium compound (a6) and/or a copper compound (a7). In addition, in the literature, there is a description that a curable composition including a radical-polymerizable monomer free of an acidic group (nonacidic monomer) and the chemical polymerization initiator has moderate curability and is excellent in long-term storage stability, and the composition shows an excellent adhesive property by being used in combination with a primer containing an acidic group-containing radical-polymerizable monomer (hereinafter sometimes referred to as "acidic monomer").

Further, in JP 2014-152106 A, as a dental curable composition that can secure a sufficient operation time for a dental treatment and is excellent in adhesive property, there is a disclosure of a dental curable composition including (A) a polymerizable monomer containing an acidic group-containing polymerizable monomer (acidic monomer), (B) a thiourea derivative, (C) a hydroperoxide-based organic peroxide, and (D) a water-soluble copper compound. In addition, in the literature, there is a description that when the dental curable composition is further blended with (E) an aryl borate compound, its curing can be accelerated to improve its adhesive strength.

Those polymerization initiators described in JP 2007-056020 A; JP 2014-227370 A; and JP 2014-152106 A are each used as a curable composition by being blended into a polymerizable monomer component or the like. However, the initiators are chemical polymerization initiators, and hence each typically need to be stored by being divided (packaged) into two or more portions. Accordingly, at the time of the division of each of the chemical polymerization initiators, the polymerizable monomer component or the like to be used in the curable composition is also divided. In addition, in general, the curable composition (adhesive composition) is formed as a combination of two or more compositions (hereinafter sometimes referred to as "partial compositions") each obtained by mixing each component of the polymerizable monomer component or the like that has been divided and each component of the chemical polymerization initiator that has been divided, and each of these partial compositions is stored (in a packaged manner). In addition, the curable composition containing all the chemical polymerization initiator components is prepared by mixing the two or more partial compositions, which are each in a state of being stored in a packaged manner, immediately before its use. Thus, the chemical polymerization initiator functions simultaneously with the mixing, and hence the curable composition polymerizes and cures.

At this time, an acid component that plays an important role in adhesion (1) may be blended into any one of the partial compositions, or (2) may be blended into any other composition except the curable composition including the combination of the two or more partial compositions (hereinafter sometimes referred to as "curing auxiliary composition") without being blended into any partial composition. In (2) the latter case, a composition in which the curing auxiliary composition and the curable composition partially mix with each other near an interface between both the compositions may be formed by using the curing auxiliary composition and the curable composition in the stated order, or by using the compositions in the reverse order. Herein, when the curable composition is a dental curable composition, the curing auxiliary composition is, for example, a pretreatment agent, such as a primer.

Although storage stability is an important factor in the chemical polymerization initiator, in the above-mentioned use form, it is important that the storage stability of each of the partial compositions each in a packaged state be high. The storage stability in each of JP 2007-056020 A and JP 2014-227370 A also means the storage stability of such packaged partial composition. In addition, in each of JP 2007-056020 A and JP 2014-227370, there is a description that the storage stability in an example corresponding to (2) the latter case, that is, the storage stability of a partial composition (free of an acid component, such as an acidic monomer) obtained by blending a nonacidic monomer with a (divided) component of the chemical polymerization initiator is high.

Meanwhile, in the dental curable composition disclosed in JP 2014-152106 A described in the foregoing, the composition including the acidic monomer and the chemical polymerization initiator, the reactivity of an acidic group of the acidic monomer is high. Accordingly, when the curable composition is packaged by being divided into two or more partial compositions, restrictions are placed on a combination of the respective components to be blended into each partial composition. In, for example, a partial composition containing a combination of the acidic monomer and the hydroperoxide-based organic peroxide, gelation occurs at the time of its long-term storage. Accordingly, the combination of such components is not preferred.

Because of such reason, in JP 2014-152106 A, there is a disclosure that the curable composition suitably includes a combination of: a partial composition (I) obtained by blending a polymerizable monomer containing at least an acidic group-containing polymerizable monomer (acidic monomer) out of (A) the polymerizable monomers and (B) the thiourea derivative in combination; and a partial composition (II) obtained by blending (C) the hydroperoxide-based organic peroxide and (D) the water-soluble copper compound in combination. In addition, in JP 2014-152106 A, there is a disclosure that when the curable composition further includes (E) the aryl borate compound, (E) the aryl borate compound is blended into the partial composition (II).

The curable composition disclosed in JP 2014-152106 A described above, in particular, the curable composition including (E) the aryl borate compound can secure an operation time suitable for a dental application, and is excellent in adhesive property and curability. Accordingly, the curable composition is useful as a dental material, such as a dental resin cement or a dental adhesive. However, in JP 2014-152106 A, there is no description of a result of an investigation on the storage stability of the curable composition. In view of the foregoing, the inventor of the present invention have made an investigation on the storage stability of the curable composition. As a result, the inventor of the present invention have confirmed that when the partial composition (II) is preserved under relatively high temperature for a long time period, its gelation occurs.

The present invention has been made in view of the above-mentioned circumstances. That is, an object of the present invention is to provide (i) such a chemical polymerization initiator that the chemical polymerization initiator is used in chemical polymerization in a system in which an acid component is present, and that under a state before use, respective components forming the chemical polymerization initiator are dividedly blended into two or more compositions (hereinafter sometimes referred to as "partial initiator compositions") maintained in a state of being incapable of chemical contact with each other, the chemical polymerization initiator having high storage stability and high polymerization activity, (ii) an adhesive composition, an adhesive composition kit, a dental material, and a dental material kit each using the chemical polymerization initiator, and (iii) a method of storing the adhesive composition.

SUMMARY

The above-mentioned object is achieved by the present invention to be described below.

That is, according to one embodiment of the present invention, there is provided a chemical polymerization initiator, including: (a) a thiourea compound; (b) a peroxyester; (c) a divalent copper compound; and (d) an aryl borate compound.

In the chemical polymerization initiator according to one embodiment of the present invention, it is preferred that (a) the thiourea compound be a compound represented by the following general formula (1):

in the formula (1), $R^1$, $R^2$, and $R^3$ each represent a hydrogen atom, a hydroxyl group, a substituted or unsubstituted alkyl group, a substituted or unsubstituted cycloalkyl group, a substituted or unsubstituted aryl group, a substituted or unsubstituted heterocyclic group, a substituted or unsubstituted acyl group, a substituted or unsubstituted aralkyl group, or a substituted or unsubstituted alkenyl group, and $R^2$ may be bonded to any group selected from $R^1$ and $R^3$ to form a ring.

In the chemical polymerization initiator according to another embodiment of the present invention, it is preferred that (b) the peroxyester be a peroxyester having a 10-hour half-life temperature of 80° C. or more.

In the chemical polymerization initiator according to another embodiment of the present invention, it is preferred that (c) the divalent copper compound contain a divalent copper atom and a ligand coordinating to the divalent copper atom, the ligand be selected from the group consisting of a halogen atom, an atomic group containing an oxygen atom, and an atomic group containing a nitrogen atom, when the ligand is the atomic group containing the oxygen atom, the atomic group containing the oxygen atom coordinate to the divalent copper atom through the oxygen atom, and when the ligand is the atomic group containing the nitrogen atom, the atomic group containing the nitrogen atom coordinate to the divalent copper atom through the nitrogen atom.

According to one embodiment of the present invention, there is provided an adhesive composition, including: (a) a thiourea compound; (b) a peroxyester; (c) a divalent copper compound; (d) an aryl borate compound; and (e) an acidic group-containing polymerizable monomer.

In the adhesive composition according to one embodiment of the present invention, it is preferred that the adhesive composition further include (f) an acidic group-free polymerizable monomer.

According to one embodiment of the present invention, there is provided an adhesive composition kit, including a combination of a first partial composition and a second partial composition in a state of being incapable of physical contact with the first partial composition, wherein an entirety of the combination of the first partial composition and the second partial composition contains at least five components formed of (a) a thiourea compound, (b) a peroxyester, (c) a divalent copper compound, (d) an aryl borate compound, and (e) an acidic group-containing polymerizable monomer, wherein the first partial composition contains, as main components, (a) the thiourea compound and (d) the aryl borate compound out of the five components, and is substantially free of an organic peroxide, and wherein the second partial composition contains, as main components, (b) the peroxyester, (c) the divalent copper compound, and (e) the acidic group-containing polymerizable monomer out of the five components, and is substantially free of a hydroperoxide.

In the adhesive composition kit according to one embodiment of the present invention, it is preferred that at least one composition selected from the first partial composition and the second partial composition further contain (f) an acidic group-free polymerizable monomer.

In the adhesive composition kit according to another embodiment of the present invention, it is preferred that at least one composition selected from the first partial composition and the second partial composition further contain at least one component selected from the group consisting of (g) a filler and (h) a solvent.

In the adhesive composition kit according to another embodiment of the present invention, it is preferred that the first partial composition be formed only of (a) the thiourea compound, (d) the aryl borate compound, (f) an acidic group-free polymerizable monomer, and (g) a filler, the second partial composition be formed only of (b) the peroxyester, (c) the divalent copper compound, (e) the acidic group-containing polymerizable monomer, (f) an acidic group-free polymerizable monomer, and (g) a filler, (a) the thiourea compound be formed only of acetylthiourea, (b) the peroxyester be formed only of t-butyl peroxy-3,5,5-trimethylhexanoate, (c) the divalent copper compound be formed only of copper(II) acetate monohydrate, and (d) the aryl borate compound be formed only of a sodium salt of tetraphenylboric acid.

In the adhesive composition kit according to another embodiment of the present invention, it is preferred that the first partial composition be formed only of (a) the thiourea compound, (d) the aryl borate compound, (f) an acidic group-free polymerizable monomer, and (g) a filler, the second partial composition be formed only of (b) the peroxyester, (c) the divalent copper compound, (e) the acidic group-containing polymerizable monomer, (f) an acidic group-free polymerizable monomer, and (g) a filler, (a) the thiourea compound be formed only of benzoylthiourea, (b) the peroxyester be formed only of t-butyl peroxy-3,5,5-trimethylhexanoate, (c) the divalent copper compound be formed only of copper(II) acetate monohydrate, and (d) the aryl borate compound be formed only of a sodium salt of tetraphenylboric acid.

According to one embodiment of the present invention, there is provided a dental material, including the adhesive composition according to the embodiment of the present invention.

According to one embodiment of the present invention, there is provided a dental material kit, including the adhesive composition kit according to the embodiment of the present invention.

According to one embodiment of the present invention, there is provided a method of storing an adhesive composition, including storing the adhesive composition according to the embodiment of the present invention under a state in which the adhesive composition is packaged into a first partial composition and a second partial composition, wherein the first partial composition contains, as main components, (a) the thiourea compound and (d) the aryl borate compound out of five components formed of (a) the thiourea compound, (b) the peroxyester, (c) the divalent copper compound, (d) the aryl borate compound, and (e) the acidic group-containing polymerizable monomer, and is substantially free of an organic peroxide, and wherein the second partial composition contains, as main components, (b) the peroxyester, (c) the divalent copper compound, and (e) the acidic group-containing polymerizable monomer out of the five components, and is substantially free of a hydroperoxide.

Advantageous Effects of Invention

According to the present invention, there can be provided (i) the chemical polymerization initiator, in which the chemical polymerization initiator is used in chemical polymerization in a system in which an acid component is present, and under a state before use, respective components forming the chemical polymerization initiator are dividedly blended into two or more partial initiator compositions maintained in a state of being incapable of chemical contact with each other, the chemical polymerization initiator having high storage stability and high polymerization activity, (ii) the adhesive composition, the adhesive composition kit, the dental material, and the dental material kit each using the chemical polymerization initiator, and (iii) the method of storing the adhesive composition can be provided.

DETAILED DESCRIPTION

1. Chemical Polymerization Initiator

A chemical polymerization initiator of this embodiment has a feature of including: (a) a thiourea compound; (b) a peroxyester; (c) a divalent copper compound; and (d) an aryl borate compound.

The chemical polymerization initiator of this embodiment is used in chemical polymerization in a system in which an acid component is present. In addition, under a state before the use of the chemical polymerization initiator, the respective components forming the chemical polymerization initiator are dividedly blended into a combination of two or more partial initiator compositions maintained in a state of being incapable of chemical contact with each other. In addition, at least one partial initiator composition selected from the two or more partial initiator compositions is present under a state of being mixed with the acid component.

The term "state of being incapable of chemical contact" as used herein means (1) a case in which one composition and another composition are in a "state of being incapable of physical contact", or (2) a case in which even when the one composition and the other composition are in a state of being capable of physical contact, unidirectional or bidirectional molecular diffusion does not occur between the one composition and the other composition. The latter case (2) is specifically, for example, a state in which in a temperature environment at the time of the storage of the chemical polymerization initiator, the one composition and the other composition are in contact with each other under a state of being completely solidified.

In addition, the term "state of being incapable of physical contact" as used herein means a state in which the one composition and the other composition are separated from each other by an inhibiting member configured to inhibit molecular diffusion between both the compositions. Although a solid member to be suitably used as a material for a container or a bag, such as a resin, glass, a metal, or a ceramic, is generally used as the inhibiting member, a liquid may be used, or a gas may be used as long as the molecular diffusion between the one composition and the other composition can be inhibited. The "state of being incapable of physical contact" is typically, for example, a state in which one kind of composition is stored under a state of being sealed in a container configured to shield ambient air and ambient light.

In order to obtain a chemical polymerization initiator having high storage stability and high polymerization activity, the inventor of the present invention have made an investigation on the typical chemical polymerization initiator (chemical polymerization initiator formed of the combination of the hydroperoxide, the thiourea compound, the copper compound, and the aryl borate compound) blended into the curable composition disclosed in JP 2014-152106 A, the composition including the acid component. As a result, the inventor of the present invention have found the following: (i) among a wide variety of organic peroxides, a peroxyester can specifically coexist with the acidic monomer in a stable manner; (ii) when the peroxyester is selected instead of the hydroperoxide in the chemical polymerization initiator disclosed in JP 2014-152106 A, and the peroxyester is used in combination with a divalent copper compound, high polymerization activity is obtained in the presence of the acid component; and (iii) high curability and/or a high adhesive property is obtained in an adhesive composition (curable composition) using a chemical polymerization initiator including such peroxyester and divalent copper compound.

In addition, the inventor of the present invention have found that in the chemical polymerization initiator of this embodiment obtained by improving the chemical polymerization initiator described in JP 2014-152106 A described above, when the chemical polymerization initiator is formed from a combination of two partial initiator compositions, and a combination of components forming each partial initiator composition is set to a specific combination, the storage stability of each partial initiator composition is improved. Herein, the combination of the partial initiator compositions by which high storage stability is obtained in the chemical polymerization initiator of this embodiment is not particularly limited. However, when the chemical polymerization initiator of this embodiment includes two or more partial initiator compositions, it is preferred that a partial initiator composition containing at least the peroxyester (limited, however, to a partial initiator composition to be mixed with the acid component) out of the plurality of kinds of partial initiator compositions be substantially free of a hydroperoxide.

From a practical viewpoint, the chemical polymerization initiator of this embodiment suitably includes a combination of two partial initiator compositions. In this case, a combination of a first partial initiator composition and a second partial initiator composition each having the following composition is particularly suitable as a combination of two partial initiator compositions by which the storage stability of the initiator can be further improved.

First Partial Initiator Composition
1. Components to be incorporated as Main Components
   (a) The thiourea compound
   (d) The aryl borate compound
2. Component to be substantially free from being incorporated
   An organic peroxide Second Partial Initiator Composition
1. Components to be incorporated as Main Components
   (b) The peroxyester
   (c) The divalent copper compound
2. Component to be substantially free from being incorporated
   A hydroperoxide Partial Initiator Composition to be mixed with Acid Component
   The second partial initiator composition Herein, when an adhesive composition or an adhesive composition kit using the chemical polymerization initiator of this embodiment is prepared, the adhesive composition or the adhesive composition kit is formed as a combination of a first partial composition containing the first partial initiator composition and a second partial composition containing the second partial initiator composition.

The term "main component" as used herein means that when the total amount of a specific component to be incorporated into the entirety of the combination of the two compositions is set to 100 mass %, 98 mass % or more of the specific component is blended only into one of the two compositions. In, for example, the case where 98 mass % of the specific component is incorporated into one composition out of the two compositions, the specific component is a main component of the one composition. In this case, the remaining amount (2 mass %) of the specific component is incorporated into the other composition out of the two compositions. Although the content of the specific component to be incorporated as a main component into one composition only needs to be 98 mass % or more, the content is preferably 99 mass % or more, more preferably 99.5 mass % or more, still more preferably 99.9 mass % or more, most preferably 100 mass %.

In addition, when the chemical polymerization initiator of this embodiment includes the combination of the two partial initiator compositions, and by extension, when the adhesive composition and the adhesive composition kit each using the chemical polymerization initiator of this embodiment each include the combination of the two partial compositions, the phrases "substantially free of an organic peroxide" and "substantially free of a peroxyester" as used herein mean contents to be described below.

That is, a case in which the first partial initiator composition and the first partial composition containing the composition are each "substantially free of an organic peroxide" means (1) a case in which the organic peroxide (oxidizing agent) is not incorporated into the partial initiator composition containing (a) the thiourea compound (i.e., a reducing agent) (and the partial composition containing the partial initiator composition) (the content of the organic peroxide is 0 mass %), or (2) a case in which a trace amount of the organic peroxide is incorporated thereinto to the extent that no clear significant difference in storage stability is found at the time of comparison to (1) the case in which the organic peroxide is not incorporated. Herein, in the case described in the (2), the content of the organic peroxide is preferably more than 0 and 1/100 or less, more preferably more than 0 and 1/500 or less in terms of molar ratio with respect to the content of (a) the thiourea compound in the partial initiator composition.

In addition, a case in which the second partial initiator composition and the second partial composition containing the composition are each "substantially free of a hydroperoxide" means (1) a case in which the hydroperoxide is not incorporated into the partial initiator composition containing at least (b) the peroxyester (and the partial composition containing the partial initiator composition and the acid component) (the content of the hydroperoxide is 0 mass %), or (2) a case in which a trace amount of the hydroperoxide is incorporated into the chemical polymerization initiator to the extent that no clear significant differences in storage stability and polymerization activity are found at the time of comparison to (1) the case in which the hydroperoxide is not incorporated. Herein, although the amount of the hydroperoxide to be incorporated in a trace amount in the (2) cannot be uniquely specified because the amount varies depending on, for example, the kind and amount of the acidic monomer in the second partial composition, for example, the amount typically falls within the range of from more than 0 to about 2/100 or less, and more preferably falls within the range of from more than 0 to about 1/300 or less in terms of molar ratio "HP/PE" between (b) the peroxyester (PE) and the hydroperoxide (HP) in the second partial initiator composition.

Although the reason why the above-mentioned high polymerization activity is obtained in the chemical polymerization initiator of this embodiment is not necessarily clear, the inventor of the present invention have assumed the reason to be as described below. First, the inventor of the present invention have confirmed that when only a monovalent copper compound is used as a copper compound, (i) the storage stability cannot be improved no matter how the various components forming the chemical polymerization initiator or the adhesive composition using the initiator are combined, and (ii) there is a tendency that a sufficient adhesive property is not obtained in the case where the first partial composition containing the first partial initiator composition and the second partial composition containing the second partial initiator composition are mixed immediately after their preparation.

It is assumed from the foregoing fact that the reason why the chemical polymerization initiator of this embodiment shows high polymerization activity is as described below. First, when the first partial initiator composition (or the first partial composition) and the second partial initiator composition (or the second partial composition) are mixed with each other, the thiourea compound is brought into contact with the divalent copper compound first to coordinate to a divalent copper atom forming the divalent copper compound, and at the same time, to reduce the divalent copper atom to monovalent. Next, a copper complex obtained by the reduction reaction and the peroxyester are brought into contact with each other to form an active coordination compound having high activity (easily generating a radical). Then, the monovalent copper atom is oxidized to divalent again by a redox reaction involving radical generation. Thus, a cyclic process in which the copper atom reduced to monovalent once is oxidized to divalent again to be reused in the formation of the active coordination compound (catalytically without being deactivated or consumed) is repeated, and hence the chemical polymerization initiator of this embodiment is assumed to show high polymerization activity.

In addition, the chemical polymerization initiator of this embodiment includes the aryl borate compound. Accordingly, in the adhesive composition (curable composition) or the adhesive composition kit (curable composition kit) including the chemical polymerization initiator of this embodiment, the curability and/or adhesive property of the adhesive composition or the adhesive composition kit can be further improved because of the aryl borate compound.

In addition, the inventor of the present invention have made an investigation, and as a result, have confirmed that the chemical polymerization initiator of this embodiment and the adhesive composition or the adhesive composition kit using the initiator are more excellent in storage stability than the chemical polymerization initiator disclosed in JP 2014-152106 A and the curable composition using the initiator are. In particular, the adhesive composition or adhesive composition kit of this embodiment including a combination of the first partial composition containing the first partial initiator composition and the second partial composition containing the second partial initiator composition shows particularly high storage stability among various possible combinations at the time of the division of the respective components forming the adhesive composition of this embodiment into two partial compositions. A main cause for the fact that the storage stability of each of the chemical polymerization initiator of this embodiment, and the adhesive composition and the adhesive composition kit each using the initiator is improved may lie in that the peroxyester having such specificity as to be "capable of stably coexisting with the acidic monomer" confirmed by the inventor of the present invention is used instead of the hydroperoxide. In addition, details about the reason why the adhesive composition and adhesive composition kit of this embodiment each including the combination of the first partial composition and the second partial composition each show storage stability higher than that of each of an adhesive composition and an adhesive composition kit each obtained by combining partial compositions different in composition from the first and second partial compositions are unclear. However, the high storage stability is assumed to result from (i) the fact that the hydroperoxide is replaced with the peroxyester, and (ii) the fact that the combination of the main components forming the first partial initiator composition (or the first partial composition) and the combination of the main components forming the second partial initiator composition (or the second partial composition) are set to specific combinations whose examples are as described above.

Next, details about (a) the thiourea compound, (b) the peroxyester, (c) the divalent copper compound, and (d) the aryl borate compound to be used in the chemical polymerization initiator of this embodiment, and any other component that may be further added as required in addition to the components (a) to (d) are described below.

(a) Thiourea Compound

Any compound may be used as the thiourea compound as long as the compound is a known thiourea compound. The thiourea compound refers to a compound having a structure "=N—C(=S)—N=".

Of such compounds, a thiourea compound represented by the following general formula (1) is preferably used.

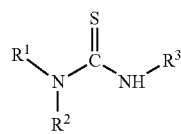

(1)

Herein, in the general formula (1), $R^1$, $R^2$, and $R^3$ each represent a hydrogen atom, a hydroxyl group, a substituted or unsubstituted alkyl group, a substituted or unsubstituted cycloalkyl group, a substituted or unsubstituted aryl group, a substituted or unsubstituted heterocyclic group, a substituted or unsubstituted acyl group, a substituted or unsubstituted aralkyl group, or a substituted or unsubstituted alkenyl group, and $R^2$ may be bonded to any group selected from $R^1$ and $R^3$ to form a ring.

The substituted or unsubstituted alkyl group, which may be any one of a linear alkyl group and a branched alkyl group, is preferably an alkyl group having 1 to 30 carbon atoms, more preferably an alkyl group having 1 to 5 carbon atoms. In addition, when a hydrogen atom forming the alkyl group is substituted with a substituent, examples of the substituent include: (a) a halogen atom, such as a fluorine atom, a chlorine atom, or a bromine atom; (b) a hydroxyl group; (c) a nitro group; (d) a cyano group; (e) an aryl group having 6 to 10 carbon atoms, such as a phenyl group, a nitrophenyl group, or a chlorophenyl group; (f) an alkoxy group having 1 to 5 carbon atoms, such as a methoxy group, an ethoxy group, or a propoxy group; (g) an acyl group having 2 to 5 carbon atoms, such as an acetyl group; and (h) a tetrahydrofuran group. In addition, although the number and positions of the substituents are not particularly limited, the number of the substituents is preferably 3 or less, more preferably 1.

The substituted or unsubstituted cycloalkyl group is preferably a cycloalkyl group that has any ring structure selected from a monocyclic structure and a polycyclic structure in which two or three monocycles are bonded to each other, and that has 3 to 14 carbon atoms (provided that a carbon atom forming a substituent is excluded from the number of carbon atoms). In addition, when a hydrogen atom forming the cycloalkyl group is substituted with a substituent, examples of the substituent include the groups (a) to (h) given as the examples of the substituent of the above-mentioned alkyl group and (i) an alkyl group having 1 to 5 carbon atoms, such as a methyl group, an ethyl group, or a butyl group. In addition, although the number and positions of the substituents are not particularly limited, the number of the substituents is preferably 3 or less, more preferably 1.

The substituted or unsubstituted aryl group is preferably an aryl group that has any ring structure selected from a monocyclic structure and a fused polycyclic structure in which two or three monocycles are fused to each other, and that has 6 to 14 carbon atoms (provided that a carbon atom forming a substituent is excluded from the number of carbon atoms). When a hydrogen atom forming the aryl group is substituted with a substituent, examples of the substituent may include the groups (a) to (i) given as the examples of the substituent of the above-mentioned cycloalkyl group. In addition, although the number and positions of the substituents are not particularly limited, the number of the substituents is preferably 3 or less, more preferably 1.

The substituted or unsubstituted heterocyclic group is preferably a heterocyclic group that has any ring structure selected from a monocyclic structure and a fused polycyclic structure in which two or three monocycles are fused to each other, and that has 3 to 14 atoms forming the skeleton of the ring structure. When a hydrogen atom forming the heterocyclic group is substituted with a substituent, examples of the substituent may include the groups (a) to (i) given as the examples of the substituent of the above-mentioned cycloalkyl group. In addition, although the number and positions of the substituents are not particularly limited, the number of the substituents is preferably 3 or less, more preferably 1.

In addition, the substituted or unsubstituted acyl group is preferably a group having 2 to 20 carbon atoms. When a hydrogen atom forming the acyl group is substituted with a substituent, examples of the substituent may include the substituents (a) to (i) given as the examples of the substituent of the above-mentioned cycloalkyl group.

In addition, the substituted or unsubstituted aralkyl group is preferably a group having 7 to 20 carbon atoms (provided that carbon forming a substituent is excluded from the number of carbon atoms). When a hydrogen atom forming the aralkyl group is substituted with a substituent, examples of the substituent may include the substituents (a) to (i) given as the examples of the substituent of the above-mentioned cycloalkyl group.

In addition, the substituted or unsubstituted alkenyl group is preferably a group having 7 to 20 carbon atoms (provided that carbon forming a substituent is excluded from the number of carbon atoms). When a hydrogen atom forming the alkenyl group is substituted with a substituent, examples of the substituent may include the substituents (a) to (i) given as the examples of the substituent of the above-mentioned cycloalkyl group.

In addition, examples of the ring to be formed by bonding of $R^1$ and $R^2$ include ethyleneimine, azacyclobutane, pyrrolidine, piperidine, and hexamethyleneimine. Examples of the ring to be formed by bonding of $R^1$ and $R^3$ include ethylenethiourea, propylenethiourea, and butylenethiourea.

Of the thiourea compounds each represented by the general formula (1), a compound in which at least two groups out of $R^1$, $R^2$, and $R^3$ are hydrogen atoms, and the remaining one group is a substituent is preferred from the viewpoint of the storage stability of the chemical polymerization initiator. For example, a thiourea compound in which $R^2$ and $R^3$ each represent a hydrogen atom, and $R^1$ represents an acyl group is most suitable.

Examples of the thiourea compound that can be suitably used may include thiourea, methylthiourea, ethylthiourea, n-propylthiourea, isopropylthiourea, cyclohexylthiourea, benzylthiourea, phenylthiourea, acetylthiourea, benzoylthiourea, adamantylthiourea, 1-(2-pyridyl)-2-thiourea, 1-(2-tetrahydrofurfuryl)-2-thiourea, N,N'-dimethylthiourea, N,N'-diethylthiourea, N,N'-di-n-propylthiourea, N,N'-diisopropylthiourea, N,N'-dicyclohexylthiourea, N,N'-diphenylthiourea, trimethylthiourea, triethylthiourea, tri-n-propylthiourea, triisopropylthiourea, tricyclohexylthiourea, tetramethylthiourea, tetraethylthiourea, tetra-n-propylthiourea, tetraisopropylthiourea, tetracyclohexylthiourea, ethylenethiourea, and 4,4'-dimethylethylenethiourea. As a specific example of the most suitable thiourea compound, there is given acetylthiourea or benzoylthiourea.

In addition, only one kind of the thiourea compounds may be used, or two or more kinds thereof may be used in combination. When two or more kinds of the thiourea compounds are used, a mass serving as a reference is the total mass of the thiourea compounds.

In the chemical polymerization initiator of this embodiment, the blending amount of (a) the thiourea compound, which is not particularly limited, is preferably set to from 4 parts by mass to 4, 800 parts by mass per 100 parts by mass of (b) the peroxyester. When the blending amount satisfies the range, the initiator can exhibit high polymerization activity and high storage stability. In order for the initiator to exhibit higher polymerization activity and higher storage stability, the blending amount is set to more preferably from 13 parts by mass to 875 parts by mass, still more preferably from 27 parts by mass to 600 parts by mass per 100 parts by mass of the peroxyester.

(b) Peroxyester (b) The peroxyester is a compound having a structure represented by R—C(=O)—O—O—R' (where R and R' each represent an arbitrary organic group) or R—O—C(=O)—O—O—R' (where R and R' each represent an arbitrary organic group). In the chemical polymerization initiator of this embodiment, a peroxyester having such structure may be used without any particular limitation. Specific examples of the peroxyester that can be suitably used may include cumyl peroxyneodecanoate, 1,1,3,3-tetramethylbutyl peroxydecanoate, t-hexyl peroxyneodecanoate, t-butyl peroxyneodecanoate, t-hexyl peroxypivalate, t-butyl peroxypivalate, 1,1,3,3-tetramethylbutyl peroxy-2-ethylhexanoate, 2,5-dimethyl-2,5-di(2-ethylhexanoylperoxy)hexane, t-hexyl peroxy-2-ethylhexanoate, t-butylperoxy-2-ethylhexanoate, t-hexyl peroxy isopropyl monocarbonate, t-butyl peroxy-3,5,5-trimethylhexanoate, t-butyl peroxylaurate, t-butyl peroxy isopropyl monocarbonate, t-butyl peroxy-2-ethylhexyl monocarbonate, t-hexyl peroxybenzoate, 2,5-di(benzoylperoxy)hexane, t-butyl peroxyacetate, t-butyl peroxy-3-methylbenzoate, and t-butyl peroxybenzoate. Of those, from the viewpoints of the polymerization activity and storage stability of the chemical polymerization initiator, a peroxyester having a 10-hour half-life temperature of 80° C. or more is suitably used, and for example, t-butyl peroxy-3,5,5-trimethylhexanoate, t-butyl peroxylaurate, t-butyl peroxy-2-ethylhexyl monocarbonate, t-butyl peroxyacetate, and t-butyl peroxybenzoate are particularly suitably used.

Only one kind of (b) the peroxyesters may be used, or two or more kinds thereof may be used in combination. When two or more kinds of (b) the peroxyesters are used, a mass serving as a reference is the total mass of (b) the peroxyesters.

(c) Divalent Copper Compound

In the chemical polymerization initiator of this embodiment, the divalent copper compound is used as a copper compound. Although a monovalent copper compound may be used in combination with the divalent copper compound in the chemical polymerization initiator of this embodiment, from the viewpoint of the storage stability of the initiator, it is preferred that only a trace amount of the monovalent copper compound be incorporated into the chemical polymerization initiator of this embodiment to the extent that the storage stability is not affected, or the compound be substantially free from being incorporated thereinto. In this case, it is particularly preferred that the monovalent copper compound be substantially free from being incorporated into the second partial initiator composition. When the monovalent copper compound is incorporated into the second partial initiator composition, the monovalent copper compound may act as a reducing agent for the peroxyester to deteriorate the storage stability.

(c) The divalent copper compound may be a hydrate or an anhydride. Examples of the divalent copper compound that can be suitably used may include copper (II) chloride, copper (II) sulfate pentahydrate, copper(II) nitrate, copper (II) trifluoromethanesulfate, copper(II) acetate monohydrate, copper(II) acetylacetonate, copper(II) naphthenate, copper(II) salicylate, copper(II) benzoate, copper(II) methacrylate, butyl phthalate copper(II), copper(II) gluconate, dichloro(1,10-phenanthroline)copper(II), copper(II) disodium ethylenediaminetetraacetate tetrahydrate, copper(II) dimethyldithiocarbamate, copper(II) diethylthiocarbamate, copper(II) hexafluoroacetylacetonate, bis(1,3-propanediamine) copper(II) dichloride, and bis(8-quinolinolato)copper(II). Only one kind of those divalent copper compounds may be used, or two or more kinds thereof may be used in combination.

Of those divalent copper compounds, such a divalent copper compound that a ligand coordinating to the divalent copper atom forming the divalent copper compound is (i) a halogen atom, (ii) an atomic group containing an oxygen atom, or (iii) an atomic group containing a nitrogen atom is preferred because of high storage stability of the chemical polymerization initiator and high activity with (a) the thiourea compound. In particular, the ligand is more preferably (ii) the atomic group containing the oxygen atom, and examples of the divalent copper compound having such ligand include copper(II) sulfate, copper(II) acetate monohydrate, and copper (II) acetylacetonate. When the ligand is (ii) the atomic group containing the oxygen atom, the atomic group containing the oxygen atom coordinates to the divalent copper atom through the oxygen atom, and when the ligand is (iii) the atomic group containing the nitrogen atom, the atomic group containing the nitrogen atom coordinates to the divalent copper atom through the nitrogen atom.

In the chemical polymerization initiator of this embodiment, the blending amount of (c) the divalent copper compound (when two or more kinds of compounds are incorporated, their total blending amount), which is not particularly limited, is preferably set to from 0.002 part by mass to 250 parts by mass per 100 parts by mass of (b) the peroxyester. When the blending amount satisfies the range, the initiator can exhibit high polymerization activity and high storage stability. In order for the initiator to exhibit higher polymerization activity and higher storage stability, the blending amount is set to more preferably from 0.008 part by mass to 20 parts by mass, still more preferably from 0.03 part by mass to 8 parts by mass per 100 parts by mass of the peroxyester.

(d) Aryl Borate Compound

Although the aryl borate compound is not particularly limited as long as the compound has at least one boron-aryl bond in a molecule thereof, a compound represented by the following general formula (2) is suitably used.

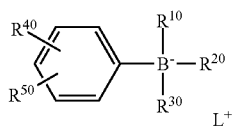
(2)

In the general formula (2), $R^{10}$, $R^{20}$, and $R^{30}$ each represent a substituted or unsubstituted alkyl group, a substituted or unsubstituted aryl group, a substituted or unsubstituted aralkyl group, or a substituted or unsubstituted alkenyl group, $R^{40}$ and $R^{50}$ each independently represent a hydrogen atom, a halogen atom, a substituted or unsubstituted alkyl group, or a substituted or unsubstituted phenyl group, and $L^+$ represents a metal cation, a quaternary ammonium ion, a quaternary pyridinium ion, a quaternary quinolinium ion, or a phosphonium ion.

In the general formula (2), the substituted or unsubstituted alkyl group selected as $R^{10}$, $R^{20}$, or $R^{30}$, which may be any one of a linear alkyl group and a branched alkyl group, is preferably a linear alkyl group having 3 to 30 carbon atoms, particularly preferably a linear alkyl group having 4 to 20 carbon atoms. In addition, when a hydrogen atom forming the alkyl group is substituted with a substituent, examples of the substituent include: (a) a halogen atom, such as a fluorine atom, a chlorine atom, or a bromine atom; (b) a hydroxyl group; (c) a nitro group; (d) a cyano group; (e) an aryl group having 6 to 10 carbon atoms, such as a phenyl group, a nitrophenyl group, or a chlorophenyl group; (f) an alkoxy group having 1 to 5 carbon atoms, such as a methoxy group, an ethoxy group, or a propoxy group; and (g) an acyl group having 2 to 5 carbon atoms, such as an acetyl group. In addition, although the number and positions of the substituents are not particularly limited, the number of the substituents is preferably 3 or less, more preferably 1.

The substituted or unsubstituted aryl group selected as $R^{10}$, $R^{20}$, or $R^{30}$ is preferably an aryl group that has any ring structure selected from a monocyclic structure and a fused polycyclic structure in which two or three monocycles are fused to each other, and that has 6 to 14 carbon atoms (provided that a carbon atom forming a substituent is excluded from the number of carbon atoms). When a hydrogen atom forming the aryl group is substituted with a substituent, examples of the substituent include the groups (a) to (g) given as the examples of the substituent of the above-mentioned alkyl group and (h) an alkyl group having 1 to 5 carbon atoms, such as a methyl group, an ethyl group, or a butyl group. In addition, although the number and positions of the substituents are not particularly limited, the number of the substituents is preferably 3 or less, more preferably 1.

The substituted or unsubstituted aralkyl group selected as $R^{10}$, $R^{20}$, or $R^{30}$ is preferably an aralkyl group having 7 to 20 carbon atoms (provided that carbon forming a substituent is excluded from the number of carbon atoms). When a hydrogen atom forming the aralkyl group is substituted with a substituent, examples of the substituent may include the groups (a) to (h) given as the examples of the substituent of the above-mentioned aryl group.

The substituted or unsubstituted alkenyl group selected as $R^{10}$, $R^{20}$, or $R^{30}$ is preferably an alkenyl group having 4 to 20 carbon atoms (provided that carbon forming a substituent is excluded from the number of carbon atoms). When a hydrogen atom forming the alkenyl group is substituted with a substituent, examples of the substituent may include the groups (a) to (g) given as the examples of the substituent of the above-mentioned alkyl group.

In the general formula (2), the substituted or unsubstituted alkyl group selected as $R^{40}$ or $R^{50}$ is preferably an alkyl group having 1 to 10 carbon atoms (provided that carbon forming a substituent is excluded from the number of carbon atoms). When a hydrogen atom forming the alkyl group is substituted with a substituent, examples of the substituent include the groups (a) to (h) given as the examples of the substituent of the alkyl group represented by any one of the groups $R^1$ to $R^3$ in the general formula (1).

In addition, when a hydrogen atom forming the substituted or unsubstituted phenyl group selected as $R^{40}$ or $R^{50}$ is substituted with a substituent, examples of the substituent include the groups (a) to (h) given as the examples of the substituent of the aryl group selected as $R^{10}$, $R^{20}$, or $R^{30}$.

In addition, $L^+$ in the general formula (2) represents, for example, a metal cation, a quaternary ammonium ion, a quaternary pyridinium ion, a quaternary quinolinium ion, or a phosphonium ion. Herein, (i) the metal cation is suitably, for example, (ia) an alkali metal cation, such as a sodium ion, a lithium ion, or a potassium ion, or (ib) an alkaline earth metal cation, such as a magnesium ion, (ii) the quaternary ammonium ion is suitably, for example, a tetrabutylammonium ion, a tetramethylammonium ion, or a tetraethylammonium ion, (iii) the quaternary pyridinium ion is suitably, for example, a methylpyridinium ion or an ethylpyridinium ion, (iv) the quaternary quinolinium ion is suitably, for example, a methylquinolinium ion, an ethylquinolinium ion, or a butylquinolinium ion, and (v) the phosphonium ion is suitably, for example, a quaternary phosphonium ion, such as a tetrabutylphosphonium ion or a methyltriphenylphosphonium ion.

Suitable examples of the aryl borate compound represented by the general formula (2) may include a sodium salt, a lithium salt, a potassium salt, a triethanolammonium salt, and a tetrabutylammonium salt of tetraphenylborate.

In the chemical polymerization initiator of this embodiment, the blending amount of (d) the aryl borate compound, which is not particularly limited, is set to preferably from 10 parts by mass to 2,000 parts by mass, particularly preferably from 30 parts by mass to 1,000 parts by mass per 100 parts by mass of (b) the peroxyester. When the blending amount is set within such range, high curability and/or a high adhesive property can be obtained at the time of the use of the chemical polymerization initiator of this embodiment in the adhesive composition or the adhesive composition kit.

Other Polymerization Accelerator

In the chemical polymerization initiator of this embodiment, any other optional component may be further used in combination with the four components described in the above-mentioned (a) to (d) as required. Examples of such optional component include an aromatic sulfinic acid compound and a barbituric acid compound serving as other polymerization accelerators except the components (a) and (d). Only one kind of those polymerization accelerators may be used, or two or more kinds thereof may be used in combination.

In the chemical polymerization initiator of this embodiment, the total blending amount of the other polymerization accelerator, that is, the aromatic sulfinic acid compound and/or the barbituric acid compound, which is not particularly limited, is set to preferably from 10 parts by mass to 2,000 parts by mass, particularly preferably from 30 parts by mass to 1,000 parts by mass per 100 parts by mass of (b) the peroxyester.

Aromatic Sulfinic Acid Compound

Examples of the aromatic sulfinic acid compound that can be suitably used may include sodium p-toluenesulfinate, sodium benzenesulfinate, and a sodium salt, a triethanolammonium salt, or a tetraethylammonium salt of 2,4,6-trimethylbenzenesulfinic acid, 2,6-dimethylbenzenesulfinic acid, 2,6-diisopropylbenzenesulfinic acid, 2,4,6-trimethylbenzenesulfinic acid, or 2,4,6-triisopropylbenzenesulfinic acid. Of those aromatic sulfinic acid salts, a benzenesulfinic acid salt and a p-toluenesulfinic acid salt are preferred because the reactivity is high and the solubility in a polymerizable monomer is high.

Barbituric Acid Compound

Examples of the barbituric acid compound that can be suitably used may include 5-butylbarbituric acid, 1,3,5-trimethylbarbituric acid, 1-cyclohexyl-5-ethylbarbituric acid, and sodium salts or calcium salts of those barbituric acids.

II. Adhesive Composition and Dental Material

The chemical polymerization initiator of this embodiment is typically utilized by being blended into a reactive composition containing an acid component, the composition being utilized for various purposes. In this case, a component (nonchemical polymerization initiator component) except the chemical polymerization initiator in the reactive composition is appropriately selected in accordance with the applications of the reactive composition. The acid component may be present in the form of, for example, an acid anhydride.

The reactive composition blended with the chemical polymerization initiator of this embodiment is particularly preferably an adhesive composition including the chemical polymerization initiator of this embodiment and (e) an acidic group-containing polymerizable monomer (acidic monomer). In normal cases, the adhesive composition of this embodiment preferably further includes, as a polymerizable monomer component, (f) an acidic group-free polymerizable monomer (nonacidic monomer) in addition to (e) the acidic group-containing polymerizable monomer. In this case, (f) the acidic group-free polymerizable monomer, which only needs to be incorporated into at least one of the first partial composition or the second partial composition, is preferably incorporated into at least the first partial composition, and may be incorporated into each of both the first partial composition and the second partial composition.

The adhesive composition of this embodiment may be suitably utilized as a dental material, and can be particularly suitably utilized as a dental cement or a dental adhesive out of such dental materials. The adhesive composition of this embodiment may further appropriately include, for example, (g) a filler or (h) a solvent as required. (g) The filler and (h) the solvent only need to be incorporated into at least one of the first partial composition or the second partial composition. Herein, when the adhesive composition of this embodiment is used as a dental cement, the adhesive composition of this embodiment preferably includes (g) the filler, and when the adhesive composition of this embodiment is used as a dental adhesive, the adhesive composition of this embodiment preferably includes (h) the solvent. The blending amounts of the respective components to be blended into the adhesive composition of this embodiment may be appropriately selected in accordance with the applications of the adhesive composition.

The adhesive composition of this embodiment is such that under a state before the use of the adhesive composition, the respective components forming the adhesive composition are dividedly blended into a combination of two or more partial compositions maintained in a state of being incapable of chemical contact with each other. In addition, when the adhesive composition is used, all the kinds of partial compositions forming the adhesive composition are mixed. In the adhesive composition of this embodiment, excellent storage stability can be secured by appropriately selecting, for example, the kinds of the components to be blended into the respective partial compositions. However, when the adhesive composition of this embodiment includes two or more partial compositions, from the viewpoint of its storage stability, it is preferred that a partial composition containing at least (b) the peroxyester and (e) the acidic group-containing polymerizable monomer out of the plurality of kinds of partial compositions be substantially free of a hydroperoxide. In addition, the adhesive composition of this embodiment has excellent curability and/or an excellent adhesive property because the adhesive composition includes the chemical polymerization initiator of this embodiment having high polymerization activity.

Although the adhesive composition of this embodiment only needs to include a combination of two or more partial compositions, in practical use, the adhesive composition suitably includes a combination of two partial compositions. Accordingly, the following description is given on the premise that the adhesive composition of this embodiment includes a combination of two partial compositions.

In this case, the combination of the partial compositions by which high storage stability is obtained in the adhesive composition of this embodiment is not particularly limited, but for example, a combination of the first partial composition and the second partial composition each having the following composition is particularly suitable.

First Partial Composition
1. Components to be incorporated as Main Components
  (a) The thiourea compound
  (d) The aryl borate compound
2. Component to be substantially free from being incorporated
  An organic peroxide Second Partial Composition
1. Components to be incorporated as Main Components
  (b) The peroxyester
  (c) The divalent copper compound
  (e) The acidic group-containing polymerizable monomer
2. Component to be substantially free from being incorporated
  A hydroperoxide (e) The acidic group-containing polymerizable monomer to be used in the adhesive composition of this embodiment including the above-mentioned combination of the first partial composition and the second partial composition is blended as a main component into the second partial composition, and is hence substantially free from being incorporated into the first partial composition. In addition, from the viewpoint of the storage stability, it is more preferred that the second partial composition be also substantially free of an organic peroxide except (b) the peroxyester and the hydroperoxide.

The phrase "substantially free of an organic peroxide except the peroxyester and the hydroperoxide" as used herein means (1) a case in which the organic peroxide except the peroxyester and the hydroperoxide (hereinafter abbreviated as "organic peroxide" or "OP" only in this paragraph) is not incorporated into the second partial composition (the content of the organic peroxide is 0 mass %), or (2) a case in which a trace amount of the organic peroxide is incorporated into the second partial composition to the extent that no clear significant differences in storage stability and polymerization activity are found at the time of comparison to (1) the case in which the organic peroxide is not incorporated. Herein, in the case described in the (2), the content of the organic peroxide (OP) (in the case of two or more kinds of organic peroxides, their total content) is set to preferably more than 0 and 2/100 or less, more preferably more than 0 and 1/300 or less in terms of molar ratio "OP/PE" with respect to the content of (b) the peroxyester (PE) contained in the second partial composition. From the same viewpoint, when both of the hydroperoxide (HP) and the organic peroxide (OP) are each incorporated in a trace amount into the second partial composition, the total content of the hydroperoxide (HP) and the organic peroxide (OP) is set to preferably more than 0 and 2/100 or less, more preferably more than 0 and 1/300 or less in terms of molar ratio "(HP+OP)/PE" with respect to the content of (b) the peroxyester (PE) contained in the second partial composition.

In addition, when the adhesive composition of this embodiment further includes (f) the acidic group-free polymerizable monomer, (g) the filler, and/or (h) the solvent, these components may be blended into only one of the first partial composition and the second partial composition, or may be blended into both of the partial compositions.

With regard to the blending amount of the chemical polymerization initiator of this embodiment in the adhesive composition of this embodiment, the initiator only needs to be used in such an effective amount that the polymerization of the polymerizable monomer component appropriately advances. In normal cases, however, <I> the amount of (a) the thiourea compound is from 0.05 part by mass to 2.5 parts by mass, the amount of (b) the peroxyester is from 0.005 part by mass to 5 parts by mass, the amount of (c) the divalent copper compound is from 0.00005 part by mass to 0.05 part by mass, and the amount of (d) the aryl borate compound is from 0.05 part by mass to 6.5 parts by mass with respect to 100 parts by mass of the polymerizable monomer component contained in the adhesive composition of this embodiment.

In addition, when the adhesive composition of this embodiment is used as a dental material (in particular, a dental cement or a dental adhesive), the following blending composition is suitable. That is, <II> the amount of (a) the thiourea compound is preferably set to from 0.15 part by mass to 2 parts by mass, the amount of (b) the peroxyester is preferably set to from 0.05 part by mass to 2.5 parts by mass, the amount of (c) the divalent copper compound is preferably set to from 0.00025 part by mass to 0.0025 part by mass, and the amount of (d) the aryl borate compound is preferably set to from 0.25 part by mass to 2.5 parts by mass with respect to 100 parts by mass of the polymerizable monomer component contained in the adhesive composition of this embodiment. The adoption of such blending amounts makes it easier to secure the curability of a cured body of the dental material and to secure the adhesive strength of the material or the mechanical strength of the cured body.

However, in the blending composition described in any one of the <I> and the <II>, the blending ratios of the respective components of the chemical polymerization initiator of this embodiment contained in the adhesive composition of this embodiment are preferably as follows: the amount of (a) the thiourea compound falls within the range of from 4 parts by mass to 4,800 parts by mass, the amount of (c) the divalent copper compound falls within the range of from 0.002 part by mass to 250 parts by mass, and the amount of (d) the aryl borate compound falls within the range of from 10 parts by mass to 2,000 parts by mass with respect to 100 parts by mass of (b) the peroxyester.

The polymerizable monomer components to be used in the adhesive composition of this embodiment are described below.

(e) Acidic Group-containing Polymerizable Monomer (Acidic Monomer)

A known polymerizable monomer having at least one acidic group and at least one radical-polymerizable unsaturated group may be used as the acidic monomer. Herein, the acidic group has the following feature: an aqueous solution or aqueous suspension of a radical-polymerizable monomer having the group shows acidity. Typical examples of the group include groups each having a hydroxyl group, such as a carboxyl group (—COOH), a sulfo group (—SO$_3$H), a phosphinico group {=P(=O)OH}, and a phosphono group {—P(=O) (OH)$_2$}. In addition to such hydroxyl group-containing acidic groups, the examples may include: an acid anhydride group having a structure obtained by the dehydration condensation of two hydroxyl group-containing acidic groups; and an acid halide group obtained by substituting a hydroxyl group of a hydroxyl group-containing acidic group with a halogen. In addition, the radical-polymerizable unsaturated group is not particularly limited, and a known group may be used. Examples thereof include a (meth)acryloyl-based group, such as a (meth)acryloyl group, a (meth)acryloyloxy group, a (meth)acryloylamino group, or a (meth)acryloylthio group, a vinyl group, an allyl group, and a styryl group.

A (meth)acrylate-based acidic group-containing polymerizable monomer is suitably used as the acidic monomer from the viewpoint of polymerizability. The (meth)acrylate-based acidic group-containing polymerizable monomer is particularly suitable when the adhesive composition is used in a dental material from the viewpoint of safety to a living organism. Only one kind of the acidic monomers may be used, or two or more kinds thereof may be used in combination.

Examples of the acidic monomer that can be suitably used may include 2-(meth)acryloyloxyethyl dihydrogen phosphate, bis[2-(meth)acryloyloxyethyl]hydrogen phosphate, 2-(meth)acryloyloxyethylphenyl hydrogen phosphate, 6-(meth)acryloyloxyhexyl dihydrogen phosphate, 6-(meth)acryloyloxyhexylphenyl hydrogen phosphate, 10-(meth)acryloyloxydecyl dihydrogen phosphate, 1,3-di(meth)acryloylpropane-2-dihydrogen phosphate, 1,3-di(meth)acryloylpropane-2-phenyl hydrogen phosphate, and bis[5-{2-(meth)acryloyloxyethoxycarbonyl}heptyl] hydrogen phosphate.

(f) Acidic Group-Free Polymerizable Monomer (Nonacidic Monomer)

The nonacidic monomer is not particularly limited as long as the monomer has at least one radical-polymerizable unsaturated group in a molecule thereof, and is free of an acidic group. A (meth)acrylate-based acidic group-free polymerizable monomer is suitably used from the viewpoint of polymerizability and the viewpoint of safety to a living organism. Only one kind of the nonacidic monomers may be used, or two or more kinds thereof may be used in combination. Examples of the nonacidic monomer that can be suitably used may include methyl (meth) acrylate, ethylene glycol di(meth)acrylate, triethylene glycol di(meth)acrylate, propylene glycol di(meth)acrylate, 2,2-bis[4-(3-methacryloyloxy)-2-hydroxypropoxyphenyl]propane, 2,2-bis(methacryloyloxypolyethoxyphenyl)propane, 2-hydroxyethyl methacrylate, 2,2,4-trimethylhexamethylenebis(2-carbamoyloxyethyl) dimethacrylate, and 1,10-decanediol di(meth) acrylate.

A cured body of the adhesive composition of this embodiment may be required to have more excellent mechanical strength like a case in which the adhesive composition is used as a dental material or the like. In this case, a bifunctional, trifunctional, or tetrafunctional radical-polymerizable monomer having a plurality of radical-polymerizable groups is preferably used as the nonacidic monomer.

The blending ratios of (e) the acidic monomer and (f) the nonacidic monomer in the polymerizable monomer components of the adhesive composition of this embodiment are not particularly limited, and for example, their blending ratios when the adhesive composition is used as a dental material are the same as those of a related-art dental material including an acidic monomer. General blending ratios in an application as a dental cement or a dental adhesive are as described below, and the ratios are also applied to the adhesive composition of this embodiment.

That is, when the adhesive composition of this embodiment is used as a dental cement, as described above, the adhesive composition generally includes (g) the filler. In addition, the composition of the polymerizable monomer components contained in the dental cement is as follows: the ratio of (e) the acidic monomer is typically 0.1 mass % or more and 50 mass % or less with respect to the total mass of the polymerizable monomer components, with the balance being (f) the nonacidic monomer; and it is preferred that the ratio of (e) the acidic monomer be 1 mass % or more and 30 mass % or less with respect thereto, with the balance being (f) the nonacidic monomer. In a dental cement adopting such composition of the polymerizable monomer components, an adhesive property to dentin can be made stronger, and adhesive durability to each of the dentin and a prosthesis formed of various materials can be further improved.

In addition, when the adhesive composition of this embodiment is used as a dental adhesive, as described above, the adhesive composition generally includes (h) the solvent. In addition, the composition of the polymerizable monomer components contained in the dental adhesive is as follows: the ratio of (e) the acidic monomer is typically 0.5 mass % or more and 50 mass % or less with respect to the total mass of the polymerizable monomer components, with the balance being (f) the nonacidic monomer; and it is preferred that the ratio of (e) the acidic monomer be 3 mass % or more and 30 mass % or less with respect thereto, with the balance being (f) the nonacidic monomer. In a dental adhesive adopting such composition of the polymerizable monomer components, an adhesive property to dentin can be made stronger, and adhesive durability to the dentin can be further improved.

Next, the blending agents that may be suitably blended into the adhesive composition of this embodiment are described.

(g) Filler

An inorganic filler, an organic filler, an organic-inorganic composite filler, or the like which has been used in a related-art dental material or the like may be utilized without any particular limitation as the filler that may be used in the adhesive composition of this embodiment. From the viewpoint of the mechanical strength of the cured body of the adhesive composition, the inorganic filler or the organic-inorganic composite filler is preferably used. Only one kind of the fillers may be used, or two or more kinds thereof may be used in combination.

The shape of the filler is not particularly limited, and the filler may have such an indefinite particulate shape as obtained by typical pulverization, or may be spherical particles. In addition, the average particle diameter of the filler, which is not particularly limited, is preferably from about 0.01 µm to about 100 µm, more preferably from about 0.1 µm to about 50 µm.

The total blending amount of (g) the filler only needs to be appropriately determined in accordance with target applications. When the filler is used in a dental material, in particular, a dental cement out of such applications, the filler is preferably blended in an amount of 65 parts by mass or more and 1,000 parts by mass or less with respect to 100 parts by mass of the polymerizable monomer components contained in the dental cement. From the viewpoints of the kneadability of the dental cement and the mechanical strength of a cured body thereof, the amount is more preferably set to 150 parts by mass or more and 400 parts by mass or less with respect to 100 parts by mass of the polymerizable monomer components contained in the dental cement.

The various fillers are described below.

Inorganic Filler

Examples of the inorganic filler that is particularly suitably used in the adhesive composition of this embodiment may include: various silicas; composite oxides each containing silicon as a constituent element, such as silica-titania and silica-zirconia; clay minerals or silicic acid salts each containing silicon as a constituent element, such as talc, montmorillonite, zeolite, and calcium silicate (the above-mentioned fillers are hereinafter referred to as silica-based fillers); and ytterbium fluoride, yttrium fluoride, silicate glass, fluoroaluminosilicate glass, lanthanum glass, barium glass, and strontium glass. Those inorganic fillers may each be used after having been subjected to a surface treatment with a surface treatment agent, such as a silane coupling agent, for enabling the filler to conform to the polymerizable monomers better to improve the mechanical strength and water resistance of a cured body to be obtained. Each of the silica-based fillers is excellent in chemical stability, and is easily subjected to a surface treatment with a silane coupling agent or the like.

Organic Filler

Examples of the organic filler that can be suitably used may include polymethyl methacrylate, polyethyl methacrylate, a methyl methacrylate-ethyl methacrylate copolymer, crosslinked polymethyl methacrylate, crosslinked polyethyl methacrylate, an ethylene-vinyl acetate copolymer, a styrene-butadiene copolymer, an acrylonitrile-styrene copolymer, and an acrylonitrile-styrene-butadiene copolymer.

Organic-Inorganic Composite Filler

An organic-inorganic composite filler obtained by compositing a polymerizable monomer that may be used as (e) the acidic monomer or (f) the nonacidic monomer and an inorganic filler with each other may be suitably used as the organic-inorganic composite filler. A method for the compositing is not particularly limited, and the filler may be solid or may have pores. From the viewpoint of the mechanical strength of the cured body of the adhesive composition, such an organic-inorganic composite filler as described in WO 2013/039169 A1, the filler being obtained by covering the surface of an inorganic aggregated particle with an organic polymer and having pores, is preferably used.

(h) Solvent

Water and/or an organic solvent may be used as the solvent. Only one kind of the solvents may be used, or two or more kinds thereof may be used in combination. The organic solvent is preferably a water-soluble organic solvent. The term "water-soluble" as used herein means that a solubility in water at 20° C. is 20 g/100 ml or more. Examples of the water-soluble organic solvent may include methanol, ethanol, propanol, isopropyl alcohol, acetone, and methyl ethyl ketone. When the water-soluble organic solvent is blended into a dental material, ethanol, propanol, isopropyl alcohol, or acetone is preferably used as the water-soluble organic solvent in consideration of harmfulness to a living organism.

The blending amount of (h) the solvent (when a plurality of kinds of solvents are used as a mixture, their total blending amount) only needs to be appropriately determined in accordance with target applications. When (h) the solvent is used in a dental material, in particular, a dental adhesive out of such applications, the amount of (h) the solvent is set to preferably 10 parts by mass or more and 800 parts by mass or less, more preferably 50 parts by mass or more and 500 parts by mass or less with respect to 100 parts by mass of the polymerizable monomer components contained in the dental adhesive. When the solvent is blended in such amount, at the time of the application of the dental adhesive to the surface of a tooth, the surface of the tooth can be sufficiently decalcified, and moderate viscosity and a moderate drying property can be obtained.

III. Adhesive Composition Kit, Dental Material Kit, and Method of Storing Adhesive Composition The main feature of the adhesive composition kit (or dental material kit) of this embodiment lies in that the adhesive composition (or dental material) of this embodiment is limited to a combination of a first partial composition and a second partial composition in a state of being incapable of physical contact with the first partial composition with a view to making the adhesive composition (or dental material) of this embodiment easier to handle. In addition, with regard to the other points, the adhesive composition kit (or dental material kit) of this embodiment may be identical to the adhesive composition (or dental material) of this embodiment. The adhesive composition kit and dental material kit of this embodiment, and a method of storing of the adhesive composition of this embodiment are described in more detail below.

The adhesive composition kit of this embodiment includes a combination of a first partial composition and a second partial composition in a state of being incapable of physical contact with the first partial composition, wherein an entirety of the combination of the first partial composition and the second partial composition contains at least five components formed of (a) a thiourea compound, (b) a peroxyester, (c) a divalent copper compound, (d) an aryl borate compound, and (e) an acidic group-containing polymerizable monomer.

Herein, the first partial composition (hereinafter sometimes referred to as "first agent") contains, as main components, (a) the thiourea compound and (d) the aryl borate compound out of the above-mentioned five components, and is substantially free of an organic peroxide. In addition, the second partial composition (hereinafter sometimes referred to as "second agent") contains, as main components, (b) the peroxyester, (c) the divalent copper compound, and (e) the acidic group-containing polymerizable monomer out of the above-mentioned five components, and is substantially free of a hydroperoxide.

It is preferred that the first partial composition contain only (a) the thiourea compound and (d) the aryl borate compound out of the above-mentioned five components, and the second partial composition contain only (b) the peroxyester, (c) the divalent copper compound, and (e) the acidic group-containing polymerizable monomer out of the above-mentioned five components.

The adhesive composition kit of this embodiment may be suitably utilized as a dental material kit, and may be particularly suitably utilized as a dental cement kit or a dental adhesive kit out of the dental material kits.

In addition, in the adhesive composition kit of this embodiment, for example, the first partial composition and the second partial composition preferably include substantially only components listed in the following composition example A, B, or C, and more preferably include only the components listed in the following composition example A, B, or C. The adhesive composition kit including substantially only the components listed in the following composition example A, B, or C, and the adhesive composition kit including only the components listed in the following composition example A, B, or C are each particularly suitable as a dental cement kit.

Composition Example A

First Partial Composition
(a) Thiourea compound
(d) Aryl borate compound
(f) Acidic group-free polymerizable monomer
(g) Filler and/or (h) solvent
Second Partial Composition
(b) Peroxyester
(c) Divalent copper compound
(e) Acidic group-containing polymerizable monomer
(f) Acidic group-free polymerizable monomer
(g) Filler and/or (h) solvent Composition Example B First Partial Composition
(a) Acetylthiourea as a thiourea compound
(d) Sodium salt of tetraphenylboric acid as an aryl borate compound
(f) Acidic group-free polymerizable monomer
(g) Filler and/or (h) solvent
Second Partial Composition
(b) t-Butyl peroxy-3,5,5-trimethylhexanoate as a peroxyester
(c) Copper (II) acetate monohydrate as a divalent copper compound
(e) Acidic group-containing polymerizable monomer
(f) Acidic group-free polymerizable monomer
(g) Filler and/or (h) solvent Composition Example C First Partial Composition
(a) Benzoylthiourea as a thiourea compound
(d) Sodium salt of tetraphenylboric acid as an aryl borate compound (f) Acidic group-free polymerizable monomer
(g) Filler and/or (h) solvent
Second Partial Composition
(b) t-Butyl peroxy-3,5,5-trimethylhexanoate as a peroxyester
(c) Copper(II) acetate monohydrate as a divalent copper compound
(e) Acidic group-containing polymerizable monomer
(f) Acidic group-free polymerizable monomer
(g) Filler and/or (h) solvent The adhesive composition kit of this embodiment is not particularly limited as long as under a state before its use (at the time of its storage), the first partial composition and the second partial composition are in a state of being incapable of physical contact with each other. However, from the viewpoint of the practicality of the kit, such as handleability, each of the first partial composition and the second partial composition is preferably stored by being loaded (packaged) into any one of various containers, such as a syringe, a bag, and a bottle. In other words, a preferred method of storing the adhesive composition of this embodiment is as follows: the adhesive composition is stored under a state of being packaged into the first partial composition and the second partial composition. In addition, at the time of the use, the first partial composition and the second partial composition are mixed with each other. Under the state before the use (at the time of the storage), the adhesive composition kit of this embodiment may of course be circulated as a product in the market.

When the chemical polymerization initiator of this embodiment contained in the adhesive composition or adhesive composition kit of this embodiment includes an aromatic sulfinic acid compound and/or a barbituric acid compound, any such compound is preferably blended into the first agent. In addition, when the adhesive composition or adhesive composition kit of this embodiment includes (g) the filler and/or (h) the solvent, any such component, which may be blended into any one of the first agent and the second agent, is preferably blended into each of both the agents because of the following reason: when the agents are mixed with each other, the agents easily conform to each other, and hence their uniformization can be easily achieved.

The composition of each of the first partial composition (first agent) and the second partial composition (second agent) is basically determined so that the composition of the adhesive composition or adhesive composition kit of this embodiment may be obtained when both the agents are mixed in equal amounts with each other {when the agents are mixed at a mixing ratio (amount of the first agent/amount of the second agent) of the first agent to the second agent of 1/1 or at a mixing percentage (100×amount of the first agent/amount of the second agent) of the first agent to the second agent of 100%}. The term "equal amounts" as used herein typically means equal amounts on a mass basis, but may mean equal amounts on a volume basis when the compositions are liquid. At this time, the blending ratios of (f) the nonacidic monomer, (g) the filler, and (h) the solvent that may be appropriately blended into the first agent and/or the second agent as required are preferably set so as to satisfy the above-mentioned conditions.

However, it may be impossible to set the mixing ratio to 1/1 depending on specific composition of the adhesive composition or adhesive composition kit of this embodiment. In such cases, it is preferred to make such a preparation that the adhesive composition or adhesive composition kit of this embodiment having expected composition is obtained when the agents are mixed at a mixing ratio except 1/1 (hereinafter also referred to as "designated mixing ratio"). In addition, when the first agent and the second agent need to be turned into uniform compositions in consideration of the solubility of each component, or the properties (e.g., paste viscosities) of the first agent and the second agent need to be turned into such properties that the agents are easy to handle, it is similarly preferred to make such a preparation that the adhesive composition or adhesive composition kit of this embodiment having expected composition is obtained when the agents are mixed at the designated mixing ratio.

The designated mixing ratio (a value obtained by representing the value in the unit of percentage is also referred to as "designated mixing percentage") only needs to be appropriately determined to the extent that the polymerization activity and operability of the adhesive composition or the adhesive composition kit are not largely impaired. However, from the viewpoint of the practicality of the composition or the kit, such as handleability or ease of product packaging, the designated mixing ratio (percentage) is as follows: the mixing ratio (first agent/second agent) on a mass basis (or a volume basis) is preferably set within the range of from 1/5 to 5/1 (mixing percentage: from 20% to 500%), and the mixing ratio is more preferably set within the range of from 1/3 to 3/1 (mixing percentage: from 33% to 300%).

The designated mixing ratio (percentage) can be displayed on a mixing ratio (percentage) information display medium. For example, (i) a product package formed of a paper box or the like, (ii) a product instruction manual provided as a paper medium and/or electronic data, (iii) a container (e.g., a bottle, a syringe, or a packaging bag) configured to store each of the first agent and the second agent under a sealed state, (iv) a product catalog provided as a paper medium and/or electronic data, or (v) a message sent to a product user by electronic mail, postal matter, or the like separately from a product may be utilized as the mixing ratio (percentage) information display medium. In addition, the designated mixing percentage may be provided to the product user by a mode except the modes described in the (i) to (v) enabling the product user to find the percentage.

In each of the adhesive composition and adhesive composition kit of this embodiment, the first agent and the second agent can each be easily prepared by weighing and mixing the respective components. Then, in the adhesive composition kit of this embodiment, the respective partial compositions (agents) thus prepared are each stored (preserved) by being loaded into a container, such as a bottle, a tube, or a syringe. Then, a mixed composition in which all the components forming the adhesive composition (or adhesive composition kit) of this embodiment are mixed can be produced by taking out and mixing required amounts of those compositions immediately before its use. A mixing method at the time of the production of the mixed composition is not particularly limited, and for example, (i) a method including applying appropriate amounts of the first agent and the second agent onto kneading paper, and kneading both the agents with a spatula, (ii) a method including simultaneously extruding the first agent and the second agent from a syringe having a mixing tip connected to its tip when the first agent and the second agent are paste-like agents, or (iii) a method including collecting the first agent and the second agent in one and the same kneading dish when the first agent and the second agent are liquid may be adopted.

The mixed composition obtained through the mixing by any such method includes all kinds of the chemical polymerization initiator components and the polymerizable monomer components, and hence polymerizes and cures immediately or with a preset operation margin time. Then, a cured body can be obtained by the polymerization and the curing. A known method may be adopted as a method of polymerizing and curing the mixed composition. For example, the following only needs to be performed: the mixed composition is applied to a site that needs to be cured, and is left at rest. In this case, the mixed composition thus applied can be sufficiently cured by holding the mixed composition in the temperature range of from 10° C. to 37° C.

EXAMPLES

The present invention is described below by way of Examples, but the present invention is not limited only to the following Examples.

1. Abbreviations of Used Substances

First, the abbreviations of substances used in chemical polymerization initiators of the respective examples and the respective comparative examples, and compositions including the initiators are described below.
(a) Thiourea Compound
AcTU; Acetylthiourea
BzTU; Benzoylthiourea
PyTU; Pyridylthiourea
(b) Peroxyester
BPT; t-Butyl peroxy-3,5,5-trimethylhexanoate
BPB; t-Butyl peroxybenzoate
BPE; t-Butyl peroxy-2-ethylhexyl monocarbonate
BPL; t-Butyl peroxylaurate
(c) Divalent Copper Compound
CuA; Copper(II) acetate monohydrate
CuAA; Copper(II) acetylacetonate
CuCl2; Copper(II) chloride
Monovalent Copper Compound
CuCl; Copper(I) chloride
Cu2SO4; Copper(I) sulfate
(d) Aryl Borate Compound
PhBNa; Sodium salt of tetraphenylboric acid
PhBTEOA; Triethanolammonium salt of tetraphenylboric acid
(e) Acidic Group-containing Polymerizable Monomer (Acidic Monomer)
MDP; 10-Methacryloxydecyl dihydrogen phosphate
SPM; Mixture obtained by mixing 2-methacryloyloxyethyl dihydrogen phosphate and bis(2-methacryloyloxyethyl) hydrogen phosphate at a molar ratio of 1:1
(f) Acidic Group-free Polymerizable Monomer (Non-acidic Monomer)
BisGMA;
2,2-Bis[4-(3-Methacryloyloxy)-2-hydroxypropoxyphenyl] propane
D-2.6E; 2,2-Bis(methacryloyloxypolyethoxyphenyl)propane 3G; Triethylene glycol dimethacrylate HEMA; 2-Hydroxyethyl methacrylate UDMA;
2,2,4-trimethylhexamethylenebis(2-carbamoyloxyethyl) dimethacrylate
(g) Filler
F1; Silica zirconia filler having an average particle diameter of 3 μm
F2; Silica zirconia filler having an average particle diameter of 0.2 μm
Organic Peroxide except Peroxyester
Hydroperoxide
CHP; Cumene hydroperoxide
TMBHP; 1,1,3,3-Tetramethylbutyl hydroperoxide
Diacyl Peroxide
BPO; Benzoyl peroxide
Others
Vanadium Compound
VOAA; Vanadium(V) oxide acetylacetonate
Amine Compound
DEPT; p-Tolyldiethanolamine

2. Examples 1 to 39 and Comparative Examples 1 to 15

Adhesive compositions of Examples 1 to 39 and Comparative Examples 1 to 15 were prepared and evaluated. Those adhesive compositions each include a filler, and the adhesive compositions of Examples 1 to 39 may each be suitably utilized as a dental cement.

Example 1

Preparation of Adhesive Composition (First Agent and Second Agent)

An adhesive composition formed of a combination of a first agent and a second agent was prepared by the following procedure. That is, first, polymerizable monomers each having the following composition were blended to prepare polymerizable monomer components for the first agent and polymerizable monomer components for the second agent (the monomers were blended so that the total amount of both the polymerizable monomer components became 100 parts by mass).
(1) Polymerizable Monomer Components for First Agent
(f) BisGMA: 30 parts by mass
(f) 3G: 20 parts by mass
(2) Polymerizable Monomer Components for Second Agent
(e) MDP: 12.5 parts by mass
(f) HEMA: 5 parts by mass
(f) D-2.6E: 20 parts by mass
(f) 3G: 12.5 parts by mass Next, the polymerizable monomer components for the first agent described in the (1) and the respective components of a chemical polymerization initiator shown in the column "First agent" of Table 1 were mixed with each other, and were completely dissolved to prepare a basic composition for the first agent. In addition, separately from the foregoing, the polymerizable monomer components for the second agent described in the (2) and the respective components of the chemical polymerization initiator shown in the column "Second agent" of Table 1 were mixed with each other, and were dissolved to prepare a basic composition for the second agent.

In Table 1, the blending ratios of the respective components of the chemical polymerization initiator at the time of its packaging into the first agent and the second agent are shown as the blending amounts of the respective components when the amount of (b) the peroxyester is set to 100 parts by mass [(a) the thiourea compound: 50 parts by mass, (c) the divalent copper compound: 0.10 part by mass, (d) the aryl borate compound: 150 parts by mass].

After that, the fillers F1 and F2 were each blended in the following amounts into the basic composition for the first agent and the basic composition for the second agent thus obtained to prepare the first agent and the second agent.

F1 (93 parts by mass in total) first agent: 46.5 parts by mass, second agent: 46.5 parts by mass
F2 (140 parts by mass in total) first agent: 70 parts by mass, second agent: 70 parts by mass The composition of each of the first agent and the second agent finally obtained is shown in Table 3. In Table 3, on the premise that the total amount of the first agent and the total amount of the second agent are mixed to prepare a mixed composition, the part (s) by mass of each component when the total mass of the polymerizable monomer components of both the agents is set to 100 parts by mass is shown. For information, in each of Examples 1 to 8 of Table 3, the blending amount of (b) the peroxyester is 1 part by mass, and hence the blending amounts of the respective components forming the chemical polymerization initiator are each equal to 1/100 of the blending amount shown in Table 1.

Various Evaluations

A mixed composition obtained by mixing the first agent and the second agent prepared as described above at a mass ratio of 1:1, and a cured body thereof were each evaluated for its adhesive strength and surface hardness. In addition, in order to examine the storage stability of each of the first agent and the second agent, an adhesive strength evaluation and a surface hardness evaluation were performed by using two kinds of adhesive compositions described in the following (a) and (b). Details about adhesive strength measurement and cured body surface hardness measurement are described below.

(a) Adhesive Composition "Immediately after Preparation"

An adhesive composition formed of a combination of the first agent and the second agent within 3 hours after its preparation.

(b) Adhesive Composition "after Storage"

An adhesive composition after its storage at 50° C. for 2 weeks under a state in which the first agent and the second agent forming the adhesive composition immediately after the preparation described in the (a) are loaded into different containers.

Adhesive Strength Measurement

A cobalt-chromium alloy plate was abraded with waterproof abrasive papers #800 and #1500 under water injection, and was then subjected to a high-pressure sandblasting treatment (involving blasting sand from a distance of from 0.5 cm to 1 cm from the plate at from 4 kgf/cm² to 5 kgf/cm²). Further, after that, the plate was subjected to ultrasonic cleaning twice with ion-exchanged water and once with acetone. Next, compressed air was blown against the surface of the plate after the cleaning to dry the plate, and then a double-sided tape having opened therein a circular hole having a diameter of 3 mm was fixed to the plate. Herein, an area in the circular hole having a diameter of 3 mm is an adhesion area. Subsequently, a mixed composition obtained by mixing the first agent and the second agent forming the adhesive composition immediately after the preparation or after the storage was applied to an end surface of a cylindrical metal attachment having a diameter of 8 mm.

Then, the circular hole of the double-sided tape and the end surface of the metal attachment having applied thereto the mixed composition were brought into press contact with each other so that their central axes coincided with each other. Thus, a test sample was obtained.

Next, the test sample was immersed in water at 37° C. for 24 hours, and then a tensile load was applied thereto by using a universal tester (MODEL AG-I, manufactured by Shimadzu Corporation) under the condition of a crosshead speed of 1 ram/min. At this time, the tensile load to be applied to the test sample was gradually increased until the adhesion surface of the test sample ruptured, and the adhesive strength of the sample was determined from the maximum load at the time of the occurrence of the rupture by using the following equation (1).

$$\text{Adhesive strength (MPa)} = \text{maximum load (N)}/\text{adhesion area (mm}^2\text{)} \quad \text{Equation (1)}$$

Measurement of Surface Hardness

The first agent and the second agent forming the adhesive composition immediately after the preparation or after the storage were mixed to provide a mixed composition. The mixed composition immediately after the mixing was immediately loaded into a polyacetal-made mold having a circular hole having a diameter of 5 mm and a thickness of 1 mm. Next, the mold having loaded thereinto the mixed composition was left to stand in a thermostat under a humid condition of 37° C. for 15 minutes. Thus, a disc-like cured body as a result of the curing of the mixed composition was obtained. Then, the cured body was immersed in water at 37° C. for 24 hours to provide a measurement sample. Next, the diagonal length d (mm) of a recess formed in the surface of the cured body was measured with a microhardness meter (MODEL MHT-1, manufactured by Matsuzawa Seiki) under the loading conditions of 100 gf and 30 seconds. At this time, the surface hardness Hv of the cured body was determined on the basis of the following equation (2).

$$Hv = 1,854.37 \times 100/d^2 \quad \text{Equation (2)}$$

Examples 2 to 39

Adhesive compositions immediately after preparation and after storage were each prepared in the same manner as in Example 1 except that in Example 1, the blending ratios of the respective components of the chemical polymerization initiator were changed to ratios shown in Table 1 or Table 2, and the acidic monomer and the nonacidic monomers to be used as polymerizable monomer components, and their blending amounts and the like were changed as shown in Table 3 (Examples 2 to 10), Table 4 (Examples 11 to 20), Table 5 (Examples 21 to 30), and Table 6 (Examples 31 to 39), followed by the measurement of the surface hardnesses and adhesive strengths of the compositions.

TABLE 1

| | Composition of chemical polymerization initiator contained in adhesive composition | | | | | | | | | | | |
|---|---|---|---|---|---|---|---|---|---|---|---|---|
| | First agent | | | | | | Second agent | | | | | |
| | (a) Thiourea compound | | (d) Aryl borate compound | | Others | | (b) Peroxyester | | (c) Divalent copper compound | | Others | |
| | Component name | Blending amount (part(s) by mass) | Component name | Blending amount (part(s) by mass) | Component name | Blending amount (part(s) by mass) | Component name | Blending amount (part(s) by mass) | Component name | Blending amount (part(s) by mass) | Component name | Blending amount (part(s) by mass) |
| Example 1 | AcTU | 50 | PhBNa | 150 | — | — | BPT | 100 | CuA | 0.10 | — | — |
| Example 2 | BzTU | 50 | PhBNa | 150 | — | — | BPT | 100 | CuA | 0.10 | — | — |
| Example 3 | PyTU | 50 | PhBNa | 150 | — | — | BPT | 100 | CuA | 0.10 | — | — |
| Example 4 | AcTU | 50 | PhBNa | 150 | — | — | BPB | 100 | CuA | 0.10 | — | — |
| Example 5 | AcTU | 50 | PhBNa | 150 | — | — | BPE | 100 | CuA | 0.10 | — | — |
| Example 6 | AcTU | 50 | PhBNa | 150 | — | — | BPL | 100 | CuA | 0.10 | — | — |
| Example 7 | AcTU | 50 | PhBNa | 150 | — | — | BPT | 100 | CuAA | 0.10 | — | — |
| Example 8 | AcTU | 50 | PhBTEOA | 150 | — | — | BPT | 100 | CuA | 0.10 | — | — |
| Example 9 | AcTU | 4,800 | PhBNa | 1,500 | — | — | BPT | 100 | CuA | 1.00 | — | — |
| Example 10 | AcTU | 875 | PhBNa | 375 | — | — | BPT | 100 | CuA | 0.25 | — | — |
| Example 11 | AcTU | 600 | PhBNa | 300 | — | — | BPT | 100 | CuA | 0.20 | — | — |
| Example 12 | AcTU | 4 | PhBNa | 30 | — | — | BPT | 100 | CuA | 0.02 | — | — |
| Example 13 | AcTU | 13 | PhBNa | 38 | — | — | BPT | 100 | CuA | 0.03 | — | — |
| Example 14 | AcTU | 27 | PhBNa | 50 | — | — | BPT | 100 | CuA | 0.03 | — | — |
| Example 15 | AcTU | 500 | PhBNa | 1,500 | — | — | BPT | 100 | CuA | 20 | — | — |
| Example 16 | AcTU | 500 | PhBNa | 1,500 | — | — | BPT | 100 | CuA | 250 | — | — |
| Example 17 | AcTU | 250 | PhBNa | 750 | — | — | BPT | 100 | CuA | 8 | — | — |
| Example 18 | AcTU | 10 | PhBNa | 30 | — | — | BPT | 100 | CuA | 0.002 | — | — |
| Example 19 | AcTU | 13 | PhBNa | 38 | — | — | BPT | 100 | CuA | 0.008 | — | — |
| Example 20 | AcTU | 17 | PhBNa | 50 | — | — | BPT | 100 | CuA | 0.033 | — | — |
| Example 21 | AcTU | 625 | PhBNa | 8,125 | — | — | BPT | 100 | CuA | 1.25 | — | — |
| Example 22 | AcTU | 125 | PhBNa | 1,500 | — | — | BPT | 100 | CuA | 0.25 | — | — |
| Example 23 | AcTU | 100 | PhBNa | 1,000 | — | — | BPT | 100 | CuA | 0.20 | — | — |
| Example 24 | AcTU | 10 | PhBNa | 6 | — | — | BPT | 100 | CuA | 0.02 | — | — |
| Example 25 | AcTU | 13 | PhBNa | 13 | — | — | BPT | 100 | CuA | 0.025 | — | — |

In the table, the part(s) by mass of each component in a chemical polymerization initiator when the amount of (b) the peroxyester is set to 100 parts by mass is shown.

TABLE 2

| | Composition of chemical polymerization initiator contained in adhesive composition | | | | | | | | | | | |
|---|---|---|---|---|---|---|---|---|---|---|---|---|
| | First agent | | | | | | Second agent | | | | | |
| | (a) Thiourea compound | | (d) Aryl borate compound | | Others | | (b) Peroxyester | | (c) Divalent copper compound | | Others | |
| | Component name | Blending amount (part(s) by mass) | Component name | Blending amount (part(s) by mass) | Component name | Blending amount (part(s) by mass) | Component name | Blending amount (part(s) by mass) | Component name | Blending amount (part(s) by mass) | Component name | Blending amount (part(s) by mass) |
| Example 26 | AcTU | 17 | PhBNa | 33 | — | — | BPT | 100 | CuA | 0.03 | — | — |
| Example 27 | AcTU | 167 | PhBNa | 2,000 | — | — | BPT | 100 | CuA | 0.33 | — | — |
| Example 28 | AcTU | 13 | PhBNa | 10 | — | — | BPT | 100 | CuA | 0.025 | — | — |
| Example 29 | AcTU | 50 | PhBNa | 150 | — | — | BPT | 100 | CuA | 0.10 | — | — |
| Example 30 | AcTU | 50 | PhBNa | 150 | — | — | BPT | 100 | CuA | 0.10 | — | — |
| Example 31 | AcTU | 50 | PhBNa | 150 | — | — | BPT | 100 | CuA | 0.10 | — | — |
| Example 32 | AcTU | 50 | PhBNa | 150 | — | — | BPT | 100 | CuA | 0.10 | — | — |
| Example 33 | AcTU | 50 | PhBNa | 150 | — | — | BPT | 100 | CuA | 0.10 | — | — |
| Example 34 | AcTU | 50 | PhBNa | 150 | — | — | BPT | 100 | CuA | 0.10 | CHP | 1 |
| Example 35 | AcTU | 50 | PhBNa | 150 | — | — | BPT | 100 | CuA | 0.10 | TMBHP | 1 |
| Example 36 | AcTU | 50 | PhBNa | 150 | — | — | BPT | 100 | CuA | 0.10 | CHP | 0.2 |
| Example 37 | AcTU | 50 | PhBNa | 150 | — | — | BPT | 100 | CuA | 0.10 | TMBHP | 0.2 |
| Example 38 | — | — | PhBNa | 150 | CuA | 0.10 | BPT | 100 | — | — | AcTU | 50 |
| Example 39 | AcTU | 50 | PhBNa | 150 | BPT | 100 | — | — | CuA | 0.10 | — | — |
| Example 40 | AcTU | 50 | PhBNa | 150 | — | — | BPT | 100 | CuA | 0.10 | — | — |
| Example 41 | AcTU | 50 | PhBNa | 150 | — | — | BPT | 100 | CuA | 0.10 | — | — |
| Example 42 | AcTU | 50 | PhBNa | 150 | — | — | BPT | 100 | CuA | 0.10 | — | — |
| Example 43 | BzTU | 50 | PhBNa | 150 | — | — | BPT | 100 | CuA | 0.10 | — | — |
| Example 44 | PyTU | 50 | PhBNa | 150 | — | — | BPT | 100 | CuA | 0.10 | — | — |
| Example 45 | AcTU | 50 | PhBNa | 150 | — | — | BPB | 100 | CuA | 0.10 | — | — |
| Example 46 | AcTU | 50 | PhBNa | 150 | — | — | BPE | 100 | CuA | 0.10 | — | — |
| Example 47 | AcTU | 50 | PhBNa | 150 | — | — | BPL | 100 | CuA | 0.10 | — | — |
| Example 48 | AcTU | 50 | PhBNa | 150 | — | — | BPT | 100 | CuAA | 0.10 | — | — |
| Example 49 | AcTU | 50 | PhBTEOA | 150 | — | — | BPT | 100 | CuA | 0.10 | — | — |
| Example 50 | — | — | PhBNa | 150 | CuA | 0.10 | BPT | 100 | — | — | AcTU | 50 |
| Example 51 | AcTU | 50 | PhBNa | 150 | BPT | 100 | — | — | CuA | 0.10 | — | — |

In the table, the part(s) by mass of each component in a chemical polymerization initiator when the amount of (b) the peroxyester is set to 100 parts by mass is shown.

TABLE 3

| | Composition of adhesive composition | | | | | | | |
|---|---|---|---|---|---|---|---|---|
| | First agent | | | | Second agent | | | |
| | (f) Acidic group-free polymerizable monomer Component (part(s) by mass) | (g) Filler Component (part(s) by mass) | (a) Thiourea compound Component (part(s) by mass) | (d) Aryl borate compound Component (part(s) by mass) | (e) (f) Polymerizable monomers Component (part(s) by mass) | (g) Filler Component (part(s) by mass) | (b) Peroxyester Component (part(s) by mass) | (c) Divalent copper compound Component (part(s) by mass) |
| Example 1 | BisGMA (30) 3G (20) | F1 (46.5) F2 (70) | AcTU (0.5) | PhBNa (1.5) | MDP (12.5) HEMA (5) D-2.6E (20) 3G (12.5) | F1 (46.5) F2 (70) | BPT (1) | CuA (0.001) |
| Example 2 | BisGMA (30) 3G (20) | F1 (46.5) F2 (70) | BzTU (0.5) | PhBNa (1.5) | MDP (12.5) HEMA (5) D-2.6E (20) 3G (12.5) | F1 (46.5) F2 (70) | BPT (1) | CuA (0.001) |
| Example 3 | BisGMA (30) 3G (20) | F1 (46.5) F2 (70) | PyTU (0.5) | PhBNa (1.5) | MDP (12.5) HEMA (5) D-2.6E (20) 3G (12.5) | F1 (46.5) F2 (70) | BPT (1) | CuA (0.001) |
| Example 4 | BisGMA (30) 3G (20) | F1 (46.5) F2 (70) | AcTU (0.5) | PhBNa (1.5) | MDP (12.5) HEMA (5) D-2.6E (20) 3G (12.5) | F1 (46.5) F2 (70) | BPB (1) | CuA (0.001) |
| Example 5 | BisGMA (30) 3G (20) | F1 (46.5) F2 (70) | AcTU (0.5) | PhBNa (1.5) | MDP (12.5) HEMA (5) D-2.6E (20) 3G (12.5) | F1 (46.5) F2 (70) | BPE (1) | CuA (0.001) |
| Example 6 | BisGMA (30) 3G (20) | F1 (46.5) F2 (70) | AcTU (0.5) | PhBNa (1.5) | MDP (12.5) HEMA (5) D-2.6E (20) 3G (12.5) | F1 (46.5) F2 (70) | BPL (1) | CuA (0.001) |
| Example 7 | BisGMA (30) 3G (20) | F1 (46.5) F2 (70) | AcTU (0.5) | PhBNa (1.5) | MDP (12.5) HEMA (5) D-2.6E (20) 3G (12.5) | F1 (46.5) F2 (70) | BPT (1) | CuAA (0.001) |
| Example 8 | BisGMA (30) 3G (20) | F1 (46.5) F2 (70) | AcTU (0.5) | PhBTEOA (1.5) | MDP (12.5) HEMA (5) D-2.6E (20) 3G (12.5) | F1 (46.5) F2 (70) | BPT (1) | CuA (0.001) |
| Example 9 | BisGMA (30) 3G (20) | F1 (46.5) F2 (70) | AcTU (4.8) | PhBNa (1.5) | MDP (12.5) HEMA (5) D-2.6E (20) 3G (12.5) | F1 (46.5) F2 (70) | BPT (0.1) | CuA (0.001) |
| Example 10 | BisGMA (30) 3G (20) | F1 (46.5) F2 (70) | AcTU (3.5) | PhBNa (1.5) | MDP (12.5) HEMA (5) D-2.6E (20) 3G (12.5) | F1 (46.5) F2 (70) | BPT (0.4) | CuA (0.001) |

In the table, the part (s) by mass of each component is a blending amount when the total amount of the polymerizable monomers in the first agent and the second agent is set to 100 parts by mass.

TABLE 4

| | Composition of adhesive composition | | | | | | | |
|---|---|---|---|---|---|---|---|---|
| | First agent | | | | Second agent | | | |
| | (f) Acidic group-free polymerizable monomer Component (part(s) by mass) | (g) Filler Component (part(s) by mass) | (a) Thiourea compound Component (part(s) by mass) | (d) Aryl borate compound Component (part(s) by mass) | (e) (f) Polymerizable monomers Component (part(s) by mass) | (g) Filler Component (part(s) by mass) | (b) Peroxyester Component (part(s) by mass) | (c) Divalent copper compound Component (part(s) by mass) |
| Example 11 | BisGMA (30) 3G (20) | F1 (46.5) F2 (70) | AcTU (3) | PhBNa (1.5) | MDP (12.5) HEMA (5) D-2.6E (20) 3G (12.5) | F1 (46.5) F2 (70) | BPT (0.5) | CuA (0.001) |
| Example 12 | BisGMA (30) 3G (20) | F1 (46.5) F2 (70) | AcTU (0.2) | PhBNa (1.5) | MDP (12.5) HEMA (5) D-2.6E (20) 3G (12.5) | F1 (46.5) F2 (70) | BPT (5) | CuA (0.001) |
| Example 13 | BisGMA (30) 3G (20) | F1 (46.5) F2 (70) | AcTU (0.5) | PhBNa (1.5) | MDP (12.5) HEMA (5) D-2.6E (20) 3G (12.5) | F1 (46.5) F2 (70) | BPT (4) | CuA (0.001) |
| Example 14 | BisGMA (30) 3G (20) | F1 (46.5) F2 (70) | AcTU (0.8) | PhBNa (1.5) | MDP (12.5) HEMA (5) D-2.6E (20) 3G (12.5) | F1 (46.5) F2 (70) | BPT (3) | CuA (0.001) |
| Example 15 | BisGMA (30) 3G (20) | F1 (46.5) F2 (70) | AcTU (0.5) | PhBNa (1.5) | MDP (12.5) HEMA (5) D-2.6E (20) 3G (12.5) | F1 (46.5) F2 (70) | BPT (0.1) | CuA (0.02) |
| Example 16 | BisGMA (30) 3G (20) | F1 (46.5) F2 (70) | AcTU (0.5) | PhBNa (1.5) | MDP (12.5) HEMA (5) D-2.6E (20) 3G (12.5) | F1 (46.5) F2 (70) | BPT (0.1) | CuA (0.25) |
| Example 17 | BisGMA (30) 3G (20) | F1 (46.5) F2 (70) | AcTU (0.5) | PhBNa (1.5) | MDP (12.5) HEMA (5) D-2.6E (20) 3G (12.5) | F1 (46.5) F2 (70) | BPT (0.2) | CuA (0.016) |
| Example 18 | BisGMA (30) 3G (20) | F1 (46.5) F2 (70) | AcTU (0.5) | PhBNa (1.5) | MDP (12.5) HEMA (5) D-2.6E (20) 3G (12.5) | F1 (46.5) F2 (70) | BPT (5) | CuA (0.0001) |
| Example 19 | BisGMA (30) 3G (20) | F1 (46.5) F2 (70) | AcTU (0.5) | PhBNa (1.5) | MDP (12.5) HEMA (5) D-2.6E (20) 3G (12.5) | F1 (46.5) F2 (70) | BPT (4) | CuA (0.0003) |
| Example 20 | BisGMA (30) 3G (20) | F1 (46.5) F2 (70) | AcTU (0.5) | PhBNa (1.5) | MDP (12.5) HEMA (5) D-2.6E (20) 3G (12.5) | F1 (46.5) F2 (70) | BPT (3) | CuA (0.001) |

In the table, the part (s) by mass of each component is a blending amount when the total amount of the polymerizable monomers in the first agent and the second agent is set to 100 parts by mass.

TABLE 5

| | Composition of adhesive composition | | | | | | | |
|---|---|---|---|---|---|---|---|---|
| | First agent | | | | Second agent | | | |
| | (f) Acidic group-free polymerizable monomer Component (part(s) by mass) | (g) Filler Component (part(s) by mass) | (a) Thiourea compound Component (part(s) by mass) | (d) Aryl borate compound Component (part(s) by mass) | (e) (f) Polymerizable monomers Component (part(s) by mass) | (g) Filler Component (part (s) by mass) | (b) Peroxyester Component (part(s) by mass) | (c) Divalent copper compound Component (part(s) by mass) |
| Example 21 | BisGMA (30) 3G (20) | F1 (46.5) F2 (70) | AcTU (0.5) | PhBNa (6.5) | MDP (12.5) HEMA (5) D-2.6E (20) 3G (12.5) | F1 (46.5) F2 (70) | BPT (0.08) | CuA (0.001) |
| Example 22 | BisGMA (30) 3G (20) | F1 (46.5) F2 (70) | AcTU (0.5) | PhBNa (6) | MDP (12.5) HEMA (5) D-2.6E (20) 3G (12.5) | F1 (46.5) F2 (70) | BPT (0.4) | CuA (0.001) |
| Example 23 | BisGMA (30) 3G (20) | F1 (46.5) F2 (70) | AcTU (0.5) | PhBNa (5) | MDP (12.5) HEMA (5) D-2.6E (20) 3G (12.5) | F1 (46.5) F2 (70) | BPT (0.5) | CuA (0.001) |
| Example 24 | BisGMA (30) 3G (20) | F1 (46.5) F2 (70) | AcTU (0.5) | PhBNa (0.3) | MDP (12.5) HEMA (5) D-2.6E (20) 3G (12.5) | F1 (46.5) F2 (70) | BPT (5) | CuA (0.001) |
| Example 25 | BisGMA (30) 3G (20) | F1 (46.5) F2 (70) | AcTU (0.5) | PhBNa (0.5) | MDP (12.5) HEMA (5) D-2.6E (20) 3G (12.5) | F1 (46.5) F2 (70) | BPT (4) | CuA (0.001) |
| Example 26 | BisGMA (30) 3G (20) | F1 (46.5) F2 (70) | AcTU (0.5) | PhBNa (1) | MDP (12.5) HEMA (5) D-2.6E (20) 3G (12.5) | F1 (46.5) F2 (70) | BPT (3) | CuA (0.001) |
| Example 27 | BisGMA (30) 3G (20) | F1 (46.5) F2 (70) | AcTU (0.5) | PhBNa (6) | MDP (12.5) HEMA (5) D-2.6E (20) 3G (12.5) | F1 (46.5) F2 (70) | BPT (0.3) | CuA (0.001) |
| Example 28 | BisGMA (30) 3G (20) | F1 (46.5) F2 (70) | AcTU (0.5) | PhBNa (0.4) | MDP (12.5) HEMA (5) D-2.6E (20) 3G (12.5) | F1 (46.5) F2 (70) | BPT (4) | CuA (0.001) |
| Example 29 | BisGMA (30) 3G (20) | F1 (46.5) F2 (70) | AcTU (0.5) | PhBNa (1.5) | MDP (12.5) D-2.6E (20) 3G (17.5) | F1 (46.5) F2 (70) | BPT (1) | CuA (0.001) |
| Example 30 | BisGMA (30) 3G (20) | F1 (46.5) F2 (70) | AcTU (0.5) | PhBNa (1.5) | MDP (12.5) HEMA (5) BisGMA (20) 3G (12.5) | F1 (46.5) F2 (70) | BPT (1) | CuA (0.001) |

In the table, the part (s) by mass of each component is a blending amount when the total amount of the polymerizable monomers in the first agent and the second agent is set to 100 parts by mass.

TABLE 6

| | Composition of adhesive composition First agent | | | | |
|---|---|---|---|---|---|
| | (f) Acidic group-free polymerizable monomer Component (part(s) by mass) | (g) Filler Component (part(s) by mass) | (a) Thiourea compound Component (part(s) by mass) | (d) Aryl borate compound Component (part(s) by mass) | Others Component (part(s) by mass) |
| Example 31 | BisGMA (30) 3G (20) | F1 (46.5) F2 (70) | AcTU (0.5) | PhBNa (1.5) | — |

TABLE 6-continued

| | | | | | |
|---|---|---|---|---|---|
| Example 32 | BisGMA (30) 3G (20) | F1 (46.5) F2 (70) | AcTU (0.5) | PhBNa (1.5) | — |
| Example 33 | BisGMA (30) 3G (20) | F1 (46.5) F2 (70) | AcTU (0.5) | PhBNa (1.5) | — |
| Example 34 | BisGMA (30) 3G (20) | F1 (46.5) F2 (70) | AcTU (0.5) | PhBNa (1.5) | — |
| Example 35 | BisGMA (30) 3G (20) | F1 (46.5) F2 (70) | AcTU (0.5) | PhBNa (1.5) | — |
| Example 36 | BisGMA (30) 3G (20) | F1 (46.5) F2 (70) | AcTU (0.5) | PhBNa (1.5) | — |
| Example 37 | BisGMA (30) 3G (20) | F1 (46.5) F2 (70) | AcTU (0.5) | PhBNa (1.5) | — |
| Example 38 | BisGMA (30) 3G (20) | F1 (46.5) F2 (70) | — | PhBNa (1.5) | CuA (0.001) |
| Example 39 | BisGMA (30) 3G (20) | F1 (46.5) F2 (70) | AcTU (0.5) | PhBNa (1.5) | BPT (1) |

Composition of adhesive composition
Second agent

| | (e) (f) Polymerizable monomers Component (part(s) by mass) | (g) Filler Component (part(s) by mass) | (b) Peroxyester Component (part(s) by mass) | (c) Divalent copper compound Component (part(s) by mass) | Others Component (part(s) by mass) |
|---|---|---|---|---|---|
| Example 31 | MDP (12.5) HEMA (5) UDMA (20) 3G (12.5) | F1 (46.5) F2 (70) | BPT (1) | CuA (0.001) | — |
| Example 32 | SPM (12.5) HEMA (5) D-2.6E (20) 3G (12.5) | F1 (46.5) F2 (70) | BPT (1) | CuA (0.001) | — |
| Example 33 | SPM (12.5) D-2.6E (20) 3G (17.5) | F1 (46.5) F2 (70) | BPT (1) | CuA (0.001) | — |
| Example 34 | MDP (12.5) HEMA (5) D-2.6E (20) 3G (12.5) | F1 (46.5) F2 (70) | BPT (1) | CuA (0.001) | CHP (0.01) |
| Example 35 | MDP (12.5) HEMA (5) D-2.6E (20) 3G (12.5) | F1 (46.5) F2 (70) | BPT (1) | CuA (0.001) | TMBPH (0.01) |
| Example 36 | MDP (12.5) HEMA (5) D-2.6E (20) 3G (12.5) | F1 (46.5) F2 (70) | BPT (1) | CuA (0.001) | CHP (0.002) |
| Example 37 | MDP (12.5) HEMA (5) D-2.6E (20) 3G (12.5) | F1 (46.5) F2 (70) | BPT (1) | CuA (0.001) | TMBPH (0.002) |
| Example 38 | MDP (12.5) HEMA (5) D-2.6E (20) 3G (12.5) | F1 (46.5) F2 (70) | BPT (1) | — | AcTU (0.5) |
| Example 39 | MDP (12.5) HEMA (5) D-2.6E (20) 3G (12.5) | F1 (46.5) F2 (70) | — | CuA (0.001) | — |

In the table, the part (s) by mass of each component is a blending amount when the total amount of the polymerizable monomers in the first agent and the second agent is set to 100 parts by mass.

Evaluation Results of Examples 1 to 39

The evaluation results of the surface hardnesses and the adhesive strengths are shown in Table 7. As shown in Table 7, the adhesive composition of Example 1 showed satisfactory results with regard to both of its surface hardness and adhesive strength at each of the following time points: immediately after the preparation; and after the storage. It was found from the results that the adhesive composition of Example 1 had excellent curability, an excellent adhesive strength, and excellent storage stability.

Similarly, each of the adhesive compositions of Examples 2 to 39 also showed satisfactory results with regard to both of its surface hardness and adhesive strength at each of the following time points: immediately after the preparation; and after the storage. It was found from the results that each of the adhesive compositions of Examples 2 to 39 also had excellent curability, an excellent adhesive strength, and excellent storage stability.

The adhesive compositions of Examples 38 and 39 are each a composition obtained by changing only the combination of the main components (a) to (e) forming the first agent and the second agent for the adhesive composition of Example 1. Although the surface hardnesses and adhesive strengths of Examples 38 and 39 immediately after the preparation are high as in Example 1, their surface hardnesses and adhesive strengths after the storage show relatively high values. The values fall within practically acceptable ranges to some extent, but are lower than those of Example 1.

TABLE 7

|  | Surface hardness (Hv) | | Adhesive strength (MPa) | |
| --- | --- | --- | --- | --- |
|  | Immediately after preparation | After storage | Immediately after preparation | After storage |
| Example 1 | 43 | 42 | 23 | 23 |
| Example 2 | 37 | 37 | 21 | 20 |
| Example 3 | 35 | 35 | 21 | 20 |
| Example 4 | 43 | 43 | 23 | 23 |
| Example 5 | 43 | 42 | 23 | 23 |
| Example 6 | 41 | 36 | 23 | 20 |
| Example 7 | 39 | 38 | 22 | 22 |
| Example 8 | 37 | 35 | 21 | 19 |
| Example 9 | 39 | 34 | 21 | 17 |
| Example 10 | 38 | 34 | 21 | 19 |
| Example 11 | 38 | 35 | 21 | 19 |
| Example 12 | 32 | 33 | 17 | 16 |
| Example 13 | 35 | 35 | 19 | 18 |
| Example 14 | 38 | 37 | 21 | 21 |
| Example 15 | 38 | 38 | 21 | 21 |
| Example 16 | 36 | 36 | 21 | 20 |
| Example 17 | 42 | 41 | 22 | 22 |
| Example 18 | 39 | 36 | 21 | 19 |
| Example 19 | 40 | 38 | 21 | 20 |
| Example 20 | 39 | 39 | 22 | 21 |
| Example 21 | 37 | 35 | 21 | 19 |
| Example 22 | 39 | 36 | 21 | 19 |
| Example 23 | 39 | 38 | 21 | 20 |
| Example 24 | 32 | 30 | 16 | 14 |
| Example 25 | 35 | 33 | 17 | 16 |
| Example 26 | 38 | 35 | 20 | 19 |
| Example 27 | 38 | 35 | 20 | 19 |
| Example 28 | 33 | 31 | 16 | 15 |
| Example 29 | 45 | 43 | 24 | 23 |
| Example 30 | 44 | 42 | 24 | 23 |
| Example 31 | 43 | 42 | 23 | 22 |
| Example 32 | 42 | 41 | 22 | 22 |
| Example 33 | 43 | 41 | 23 | 22 |
| Example 34 | 40 | 35 | 22 | 19 |
| Example 35 | 41 | 35 | 22 | 19 |
| Example 36 | 42 | 37 | 22 | 20 |
| Example 37 | 42 | 36 | 22 | 19 |
| Example 38 | 42 | 31 | 22 | 15 |
| Example 39 | 41 | 30 | 21 | 15 |

Comparative Examples 1 to 4 [Examples in Each of which Chemical Polymerization Initiator Lacks any One of Components (a) to (d)]

Adhesive compositions immediately after preparation and after storage were each prepared in the same manner as in Example 1 except that in Example 1, the components of the chemical polymerization initiator to be used and their blending ratios were changed to components and ratios shown in Table 8, and the acidic monomer and the nonacidic monomers to be used as polymerizable monomer components, and their blending amounts were changed as shown in Table 9, followed by the measurement of the surface hardnesses of the compositions.

Comparative Examples 5 to 8 [Examples in Each of which Monovalent Copper Compound is Used Instead of Divalent Copper Compound]

The preparation of first agents and second agents, and the preparation of adhesive compositions were performed in the same manner as in Example 1 except that in Example 1, the components of the chemical polymerization initiator to be used and their blending ratios were changed to components and ratios shown in Table 8, and the acidic monomer and the nonacidic monomers to be used as polymerizable monomer components, and their blending amounts were changed as shown in Table 9. Thus, adhesive compositions immediately after preparation and after storage were prepared, followed by the measurement of their surface hardnesses.

Comparative Examples 9 to 12 [Examples in Each of which Hydroperoxide is Used Instead of Component (b)]

Adhesive compositions immediately after preparation and after storage were each prepared in the same manner as in Example 1 except that in Example 1, the components of the chemical polymerization initiator to be used and their blending ratios were changed to components and ratios shown in Table 8, and the acidic monomer and the nonacidic monomers to be used as polymerizable monomer components, and their blending amounts were changed as shown in Table 9 and Table 10, followed by the measurement of the surface hardnesses of the compositions.

Comparative Examples 9 and 10 are each merely an example in which a hydroperoxide is used instead of (b) the peroxyester, Comparative Example 11 is an example in which a hydroperoxide used instead of (b) the peroxyester is blended not into the second agent but into the first agent, and Comparative Example 12 is an example in which (a) the thiourea compound is removed from Comparative Example 11.

Comparative Examples 13 to 15

Adhesive compositions immediately after preparation and after storage were each prepared in the same manner as in Example 1 except that in Example 1, the components of the chemical polymerization initiator to be used and their blending ratios were changed to components and ratios shown in Table 8, and the acidic monomer and the nonacidic monomers to be used as polymerizable monomer components, and their blending amounts were changed as shown in Table 10, followed by the measurement of the surface hardnesses of the compositions.

Comparative Example 13 is an example in which the diacyl peroxide is used instead of (b) the peroxyester, Comparative Example 14 is an example in which the vanadium compound is blended instead of (c) the divalent copper compound, and Comparative Example 15 is an example in which an initiator formed of benzoyl peroxide and the amine compound is used as a chemical polymerization initiator.

TABLE 8

Composition of chemical polymerization initiator contained in adhesive composition

| | First agent | | | | | | Second agent | | | | | |
|---|---|---|---|---|---|---|---|---|---|---|---|---|
| | (a) Thiourea compound | | (d) Aryl borate compound | | Others | | Organic peroxide | | Copper compound | | Others | |
| | Component | Blending amount (part(s) by mass) | Component | Blending amount (part(s) by mass) | Component | Blending amount (part(s) by mass) | Component | Blending amount (part(s) by mass) | Component | Blending amount (part(s) by mass) | Component | Blending amount (part(s) by mass) |
| Comparative Example 1 | — | — | PhBNa | 150 | — | — | BPT | 100 | CuA | 0.1 | — | — |
| Comparative Example 2 | AcTU | — | PhBNa | — | — | — | — | — | CuA | — | — | — |
| Comparative Example 3 | AcTU | 50 | PhBNa | 150 | — | — | BPT | 100 | — | — | — | — |
| Comparative Example 4 | AcTU | 50 | — | — | — | — | BPT | 100 | CuA | 0.1 | — | — |
| Comparative Example 5 | AcTU | 50 | PhBNa | 150 | — | — | BPT | 100 | CuCl | 0.1 | — | — |
| Comparative Example 6 | AcTU | 50 | PhBNa | 150 | — | — | BPT | 100 | CuSO4 | 0.1 | — | — |
| Comparative Example 7 | AcTU | 50 | PhBNa | 150 | CuCl | 0.1 | BPT | 100 | — | — | — | — |
| Comparative Example 8 | AcTU | 50 | PhBNa | 150 | CuSO4 | 0.1 | BPT | 100 | — | — | — | — |
| Comparative Example 9 | AcTU | 50 | PhBNa | 150 | — | — | CHP | 100 | CuA | 0.1 | — | — |
| Comparative Example 10 | AcTU | 50 | PhBNa | 150 | — | — | TMBHP | 100 | CuA | 0.1 | — | — |
| Comparative Example 11 | AcTU | 50 | PhBNa | 150 | CHP | 100 | — | — | CuA | 0.1 | — | — |
| Comparative Example 12 | — | — | PhBNa | 150 | CHP | 100 | — | — | CuA | 0.1 | — | — |
| Comparative Example 13 | AcTU | 50 | PhBNa | 150 | — | — | BPO | 100 | CuA | 0.1 | — | — |
| Comparative Example 14 | AcTU | 50 | PhBNa | 150 | — | — | BPT | 100 | — | — | VOAA | 1 |
| Comparative Example 15 | — | — | — | — | BPO | 100 | — | — | — | — | DEPT | 100 |
| Comparative Example 16 | — | — | PhBNa | 150 | — | — | BPT | 100 | CuA | 0.1 | — | — |
| Comparative Example 17 | AcTU | — | PhBNa | — | — | — | — | — | CuA | — | — | — |
| Comparative Example 18 | AcTU | 50 | PhBNa | 150 | — | — | BPT | 100 | — | — | — | — |
| Comparative Example 19 | AcTU | 50 | — | — | — | — | BPT | 100 | CuA | 0.1 | — | — |

*1 In a comparative example in which (b) the peroxyester was used as an organic peroxide, the blending amount of each of the other components was shown while the blending amount of (b) the peroxyester was set to 100 parts by mass.
*2 In a comparative example in which an organic peroxide except (b) the peroxyester was used as an organic peroxide, the blending amount of each of the other components was shown while the blending amount of the organic peroxide was set to 100 parts by mass.
*3 With regard to a component that was not blended, the symbol "—" was shown in each of the columns "Component" and "Blending amount".

TABLE 9

Composition of adhesive composition
First agent

| | (f) Acidic group-free polymerizable monomer Component (part(s) by mass) | (g) Filler Component (part(s) by mass) | (a) Thiourea compound Component (part(s) by mass) | (d) Aryl borate compound Component (part(s) by mass) | Others Component (part(s) by mass) |
|---|---|---|---|---|---|
| Comparative Example 1 | BisGMA (30) 3G (20) | F1 (46.5) F2 (70) | — | PhBNa (1.5) | — |
| Comparative Example 2 | BisGMA (30) 3G (20) | F1 (46.5) F2 (70) | AcTU (0.5) | PhBNa (1.5) | — |
| Comparative Example 3 | BisGMA (30) 3G (20) | F1 (46.5) F2 (70) | AcTU (0.5) | PhBNa (1.5) | — |
| Comparative Example 4 | BisGMA (30) 3G (20) | F1 (46.5) F2 (70) | AcTU (0.5) | — | — |

TABLE 9-continued

| | | | | |
|---|---|---|---|---|
| Comparative Example 5 | BisGMA (30) 3G (20) | F1 (46.5) F2 (70) | AcTU (0.5) | PhBNa (1.5) | — |
| Comparative Example 6 | BisGMA (30) 3G (20) | F1 (46.5) F2 (70) | AcTU (0.5) | PhBNa (1.5) | — |
| Comparative Example 7 | BisGMA (30) 3G (20) | F1 (46.5) F2 (70) | AcTU (0.5) | PhBNa (1.5) | CuCl (0.001) |
| Comparative Example 8 | BisGMA (30) 3G (20) | F1 (46.5) F2 (70) | AcTU (0.5) | PhBNa (1.5) | CuSO4 (0.001) |
| Comparative Example 9 | BisGMA (30) 3G (20) | F1 (46.5) F2 (70) | AcTU (0.5) | PhBNa (1.5) | — |
| Comparative Example 10 | BisGMA (30) 3G (20) | F1 (46.5) F2 (70) | AcTU (0.5) | PhBNa (1.5) | — |

| | Composition of adhesive composition Second agent | | | | |
|---|---|---|---|---|---|
| | (e) (f) Polymerizable monomers Component (part(s) by mass) | (g) Filler Component (part(s) by mass) | Organic peroxide Component (part(s) by mass) | Copper compound Component (part(s) by mass) | Others Component (part(s) by mass) |
| Comparative Example 1 | MDP (12.5) HEMA (5) D-2.6E (20) 3G (12.5) | F1 (46.5) F2 (70) | BPT (1) | CuA (0.001) | — |
| Comparative Example 2 | MDP (12.5) HEMA (5) D-2.6E (20) 3G (12.5) | F1 (46.5) F2 (70) | — | CuA (0.001) | — |
| Comparative Example 3 | MDP (12.5) HEMA (5) D-2.6E (20) 3G (12.5) | F1 (46.5) F2 (70) | BPT (1) | — | — |
| Comparative Example 4 | MDP (12.5) HEMA (5) D-2.6E (20) 3G (12.5) | F1 (46.5) F2 (70) | BPT (1) | CuA (0.001) | — |
| Comparative Example 5 | MDP (12.5) HEMA (5) D-2.6E (20) 3G (12.5) | F1 (46.5) F2 (70) | BPT (1) | CuCl (0.001) | — |
| Comparative Example 6 | MDP (12.5) HEMA (5) D-2.6E (20) 3G (12.5) | F1 (46.5) F2 (70) | BPT (1) | CuSO4 (0.001) | — |
| Comparative Example 7 | MDP (12.5) HEMA (5) D-2.6E (20) 3G (12.5) | F1 (46.5) F2 (70) | BPT (1) | — | — |
| Comparative Example 8 | MDP (12.5) HEMA (5) D-2.6E (20) 3G (12.5) | F1 (46.5) F2 (70) | BPT (1) | — | — |
| Comparative Example 9 | MDP (12.5) HEMA (5) D-2.6E (20) 3G (12.5) | F1 (46.5) F2 (70) | CHP (1) | CuA (0.001) | — |
| Comparative Example 10 | MDP (12.5) HEMA (5) D-2.6E (20) 3G (12.5) | F1 (46.5) F2 (70) | TMBHP (1) | CuA (0.001) | — |

*1 The part(s) by mass of each component is a blending amount when the total amount of the polymerizable monomers in the first agent and the second agent is set to 100 parts by mass.
*2 With regard to a component that was not blended, the symbol "—" was shown in the column "Component".

TABLE 10

| | Composition of adhesive composition First agent | | | | |
|---|---|---|---|---|---|
| | (f) Acidic group-free polymerizable monomer Component (part(s) by mass) | (g) Filler Component (part(s) by mass) | (a) Thiourea compound Component (part(s) by mass) | (d) Aryl borate compound Component (part(s) by mass) | Others Component (part(s) by mass) |
| Comparative Example 11 | BisGMA (30) 3G (20) | F1 (46.5) F2 (70) | AcTU (0.5) | PhBNa (1.5) | CHP (1) |
| Comparative Example 12 | BisGMA (30) 3G (20) | F1 (46.5) F2 (70) | — | PhBNa (1.5) | CHP (1) |
| Comparative Example 13 | BisGMA (30) 3G (20) | F1 (46.5) F2 (70) | AcTU (0.5) | PhBNa (1.5) | — |
| Comparative Example 14 | BisGMA (30) 3G (20) | F1 (46.5) F2 (70) | AcTU (0.5) | PhBNa (1.5) | — |
| Comparative Example 15 | BisGMA (30) 3G (20) | F1 (46.5) F2 (70) | — | — | BPO (1.5) |

| | Composition of adhesive composition Second agent | | | | |
|---|---|---|---|---|---|
| | (e) (f) Polymerizable monomers Component (part(s) by mass) | (g) Filler Component (part(s) by mass) | Organic peroxide Component (part(s) by mass) | Copper compound Component (part(s) by mass) | Others Component (part(s) by mass) |
| Comparative Example 11 | MDP (12.5) HEMA (5) D-2.6E (20) 3G (12.5) | F1 (46.5) F2 (70) | — | CuA (0.001) | — |
| Comparative Example 12 | MDP (12.5) HEMA (5) D-2.6E (20) 3G (12.5) | F1 (46.5) F2 (70) | — | CuA (0.001) | — |
| Comparative Example 13 | MDP (12.5) HEMA (5) D-2.6E (20) 3G (12.5) | F1 (46.5) F2 (70) | BPO (1) | CuA (0.001) | — |
| Comparative Example 14 | MDP (12.5) HEMA (5) D-2.6E (20) 3G (12.5) | F1 (46.5) F2 (70) | BPT (1) | — | VOAA (0.01) |
| Comparative Example 15 | MDP (12.5) HEMA (5) D-2.6E (20) 3G (12.5) | F1 (46.5) F2 (70) | — | — | DEPT (1.5) |

*1 The part(s) by mass of each component is a blending amount when the total amount of the polymerizable monomers in the first agent and the second agent is set to 100 parts by mass.
*2 With regard to a component that was not blended, the symbol "—" was shown in the column "Component".

Evaluation Results of Comparative Examples 1 to 15

The evaluation results of the surface hardnesses are shown in Table 11. As shown in Table 11, in each of Comparative Examples 1 to 4, the adhesive composition did not sufficiently cure, or even when the composition cured, its surface hardness was low and insufficient. In each of Comparative Examples 5 to 8, the gelation of the first agent occurred, or even when the adhesive composition cured, its surface hardness largely reduced after the storage, and hence its storage stability was low. In each of Comparative Examples 9 to 11, the second agent gelled in the case of the adhesive composition after the storage, and hence the storage stability of the composition was low.

In addition, in Comparative Example 12, no gelation occurred, but the adhesive composition did not show a sufficient surface hardness immediately after the preparation. Moreover, the surface hardness significantly reduced after the storage as compared to that immediately after the preparation. In Comparative Example 13, the storage stability of the adhesive composition was insufficient, and in Comparative Example 14, the second agent gelled immediately after the preparation. In Comparative Example 15, the amine compound was neutralized by the acidic component, and hence the adhesive composition did not sufficiently cure even immediately after the preparation.

TABLE 11

| | Surface hardness | |
|---|---|---|
| | Immediately after preparation | After storage |
| Comparative Example 1 | No curing | No curing |
| Comparative Example 2 | 4 | 4 |
| Comparative Example 3 | No curing | No curing |
| Comparative Example 4 | 23 | 22 |
| Comparative Example 5 | 43 | 28 |
| Comparative Example 6 | 42 | 28 |
| Comparative Example 7 | First agent gelled | First agent gelled |
| Comparative Example 8 | First agent gelled | First agent gelled |
| Comparative Example 9 | 39 | Second agent gelled |
| Comparative Example 10 | 41 | Second agent gelled |
| Comparative Example 11 | First agent gelled | First agent gelled |
| Comparative Example 12 | 21 | 14 |
| Comparative Example 13 | 32 | Second agent gelled |
| Comparative Example 14 | Second agent gelled | Second agent gelled |
| Comparative Example 15 | No curing | Second agent gelled |

3. Examples 40 to 51 and Comparative Examples 16 to 19

Adhesive compositions of Examples 40 to 51 and Comparative Examples 16 to 19 were prepared and evaluated. Those adhesive compositions each include a solvent, and the adhesive compositions of Examples 40 to 51 may each be suitably utilized as a dental adhesive.

Examples 40 to 51

Adhesive compositions immediately after preparation and after storage were each prepared in the same manner as in Example 1 except that in Example 1, the blending ratios of the respective components of the chemical polymerization initiator were changed to ratios shown in Table 2, and the acidic monomer and the nonacidic monomers to be used as polymerizable monomer components, and their blending amounts and the like were changed as shown in Table 12, followed by the measurement of the surface hardnesses and adhesive strengths of the compositions. However, a test sample for adhesive strength measurement was produced by: applying a mixed composition obtained by mixing the first agent and the second agent to the inside of the circular hole of the double-sided tape; then blowing compressed air against the applied composition to remove its solvent; and bringing the circular hole of the double-sided tape and the end surface of the metal attachment having applied thereto the mixed composition into press contact with each other after the removal so that their central axes coincided with each other. Each of those examples is an example in which a solvent is used, and is intended for use in an application where a high surface hardness is not required (application where a cured body layer is thin and only an adhesive force is required).

Comparative Examples 16 to 19

Adhesive compositions immediately after preparation and after storage were each prepared in the same manner as in Example 1 except that in Example 40, the components of the chemical polymerization initiator to be used and their blending ratios were changed to components and ratios shown in Table 8, and the acidic monomer and the nonacidic monomers to be used as polymerizable monomer components, and their blending amounts and the like were changed as shown in Table 13, followed by the measurement of the surface hardnesses and adhesive strengths of the compositions.

TABLE 12

| | Composition of adhesive composition First agent | | | | |
|---|---|---|---|---|---|
| | (f) Acidic group-free polymerizable monomer Component (part(s) by mass) | (h) Solvent Component (part(s) by mass) | (a) Thiourea compound Component (part(s) by mass) | (d) Aryl borate compound Component (part(s) by mass) | Others Component (part(s) by mass) |
| Example 40 | BisGMA (30) 3G (20) | Ethanol (50) | AcTU (0.5) | PhBNa (1.5) | — |
| Example 41 | BisGMA (30) 3G (20) | Acetone (50) | AcTU (0.5) | PhBNa (1.5) | — |
| Example 42 | BisGMA (30) 3G (20) | Ethanol (50) Water (10) | AcTU (0.5) | PhBNa (1.5) | — |
| Example 43 | BisGMA (30) 3G (20) | Ethanol (50) Water (10) | BzTU (0.5) | PhBNa (1.5) | — |
| Example 44 | BisGMA (30) 3G (20) | Ethanol (50) Water (10) | PyTU (0.5) | PhBNa (1.5) | — |
| Example 45 | BisGMA (30) 3G (20) | Ethanol (50) Water (10) | AcTU (0.5) | PhBNa (1.5) | — |
| Example 46 | BisGMA (30) 3G (20) | Ethanol (50) Water (10) | AcTU (0.5) | PhBNa (1.5) | — |
| Example 47 | BisGMA (30) 3G (20) | Ethanol (50) Water (10) | AcTU (0.5) | PhBNa (1.5) | — |

TABLE 12-continued

| | | | | | |
|---|---|---|---|---|---|
| Example 48 | BisGMA (30) 3G (20) | Ethanol (50) Water (10) | AcTU (0.5) | PhBNa (1.5) | — |
| Example 49 | BisGMA (30) 3G (20) | Ethanol (50) Water (10) | AcTU (0.5) | PhBTEOA (1.5) | — |
| Example 50 | BisGMA (30) 3G (20) | Ethanol (50) Water (10) | — | PhBNa (1.5) | CuA (0.001) |
| Example 51 | BisGMA (30) 3G (20) | Ethanol (50) Water (10) | AcTU (0.5) | PhBNa (1.5) | BPT (1) |

| | Composition of adhesive composition Second agent | | | | |
|---|---|---|---|---|---|
| | (e) (f) Polymerizable monomers Component (part(s) by mass) | (h) Solvent Component (part(s) by mass) | (b) Peroxyester Component (part(s) by mass) | (c) Divalent copper compound Component (part(s) by mass) | Others Component (part(s) by mass) |
| Example 40 | MDP (12.5) HEMA (5) D-2.6E (20) 3G (12.5) | Ethanol (50) | BPT (1) | CuA (0.001) | — |
| Example 41 | MDP (12.5) HEMA (5) D-2.6E (20) 3G (12.5) | Acetone (50) | BPT (1) | CuA (0.001) | — |
| Example 42 | MDP (12.5) HEMA (5) D-2.6E (20) 3G (12.5) | Ethanol (50) | BPT (1) | CuA (0.001) | — |
| Example 43 | MDP (12.5) HEMA (5) D-2.6E (20) 3G (12.5) | Ethanol (50) | BPT (1) | CuA (0.001) | — |
| Example 44 | MDP (12.5) HEMA (5) D-2.6E (20) 3G (12.5) | Ethanol (50) | BPT (1) | CuA (0.001) | — |
| Example 45 | MDP (12.5) HEMA (5) D-2.6E (20) 3G (12.5) | Ethanol (50) | BPB (1) | CuA (0.001) | — |
| Example 46 | MDP (12.5) HEMA (5) D-2.6E (20) 3G (12.5) | Ethanol (50) | BPE (1) | CuA (0.001) | — |
| Example 47 | MDP (12.5) HEMA (5) D-2.6E (20) 3G (12.5) | Ethanol (50) | BPL (1) | CuA (0.001) | — |
| Example 48 | MDP (12.5) HEMA (5) D-2.6E (20) 3G (12.5) | Ethanol (50) | BPT (1) | CuAA (0.001) | — |
| Example 49 | MDP (12.5) HEMA (5) D-2.6E (20) 3G (12.5) | Ethanol (50) | BPT (1) | CuA (0.001) | — |
| Example 50 | MDP (12.5) HEMA (5) D-2.6E (20) 3G (12.5) | Ethanol (50) | BPT (1) | — | AcTU (0.5) |
| Example 51 | MDP (12.5) HEMA (5) D-2.6E (20) 3G (12.5) | Ethanol (50) | — | CuA (0.001) | — |

In the table, the part (s) by mass of each component is a blending amount when the total amount of the polymerizable monomers in the first agent and the second agent is set to 100 parts by mass.

TABLE 13

| | Composition of adhesive composition First agent | | | | |
|---|---|---|---|---|---|
| | (f) Acidic group-free polymerizableable monomer Component (part(s) by mass) | (h) Solvent Component (part(s) by mass) | (a) Thiourea compound Component (part(s) by mass) | (d) Aryl borate compound Component (part(s) by mass) | Others Component (part(s) by mass) |
| Comparative Example 16 | BisGMA (30) 3G (20) | Ethanol (50) | — | PhBNa (1.5) | — |
| Comparative Example 17 | BisGMA (30) 3G (20) | Ethanol (50) | AcTU (0.5) | PhBNa (1.5) | — |
| Comparative Example 18 | BisGMA (30) 3G (20) | Ethanol (50) | AcTU (0.5) | PhBNa (1.5) | — |
| Comparative Example 19 | BisGMA (30) 3G (20) | Ethanol (50) | AcTU (0.5) | — | — |

| | Composition of adhesive composition Second agent | | | | |
|---|---|---|---|---|---|
| | (e) (f) Polymerizable monomers Component (part(s) by mass) | (h) Solvent Component (part(s) by mass) | Organic peroxide Component (part(s) by mass) | Copper compound Component (part(s) by mass) | Others Component (part(s) by mass) |
| Comparative Example 16 | MDP (12.5) HEMA (5) D-2.6E (20) 3G (12.5) | Ethanol (50) | BPT (1) | CuA (0.001) | — |
| Comparative Example 17 | MDP (12.5) HEMA (5) D-2.6E (20) 3G (12.5) | Ethanol (50) | — | CuA (0.001) | — |
| Comparative Example 18 | MDP (12.5) HEMA (5) D-2.6E (20) 3G (12.5) | Ethanol (50) | BPT (1) | — | — |
| Comparative Example 19 | MDP (12.5) HEMA (5) D-2.6E (20) 3G (12.5) | Ethanol (50) | BPT (1) | CuA (0.001) | — |

*1 The part(s) by mass of each component is a blending amount when the total amount of the polymerizable monomers in the first agent and the second agent is set to 100 parts by mass.
*2 With regard to a component that was not blended, the symbol "—" was shown in the column "Component".

Evaluation Results of Examples 40 to 51 and Comparative Examples 16 to 19

The measurement results of the surface hardnesses and adhesive strengths of Examples 40 to 51, and the measurement results of the surface hardnesses of Comparative Examples 16 to 19 are shown in Table 14. As shown in Table 14, each of the adhesive compositions of Examples 40 to 51 showed a satisfactory result with regard to both of its adhesive strength and surface hardness at each of the following time points: immediately after the preparation; and after the storage.

Meanwhile, in each of Comparative Examples 16 to 19, the adhesive composition did not sufficiently cure, or even when the composition cured, its surface hardness was low and insufficient. Accordingly, adhesive strength measurement was not performed. In addition, in Comparative Example 19, adhesive strength measurement was attempted because the composition cured, though its surface hardness was low. However, in Comparative Example 19, no specific value could be measured because the composition had so low an adhesive strength as to be easily removed from the metal attachment with a hand immediately after the preparation.

TABLE 14

| | Surface hardness (Hv) | | Adhesive strength (MPa) | |
|---|---|---|---|---|
| | Immediately after preparation | After storage | Immediately after preparation | After storage |
| Example 40 | 13 | 13 | 23 | 23 |
| Example 41 | 13 | 13 | 23 | 23 |
| Example 42 | 13 | 13 | 23 | 23 |
| Example 43 | 10 | 10 | 21 | 21 |
| Example 44 | 8 | 8 | 21 | 21 |
| Example 45 | 13 | 13 | 23 | 23 |
| Example 46 | 13 | 11 | 23 | 22 |

TABLE 14-continued

|  | Surface hardness (Hv) | | Adhesive strength (MPa) | |
| --- | --- | --- | --- | --- |
|  | Immediately after preparation | After storage | Immediately after preparation | After storage |
| Example 47 | 12 | 10 | 23 | 21 |
| Example 48 | 11 | 11 | 22 | 22 |
| Example 49 | 10 | 10 | 20 | 18 |
| Example 50 | 13 | 5 | 22 | 15 |
| Example 51 | 13 | 5 | 22 | 16 |
| Comparative Example 16 | No curing | No curing | — | — |
| Comparative Example 17 | Unmeasurable | Unmeasurable | — | — |
| Comparative Example 18 | No curing | No curing | — | — |
| Comparative Example 19 | 2 | 2 | Unmeasurable | Unmeasurable |

The invention claimed is:

1. A chemical polymerization initiator, comprising:
(a) a thiourea compound;
(b) a peroxyester;
(c) a divalent copper compound; and
(d) an aryl borate compound.

2. The chemical polymerization initiator according to claim 1, wherein (a) the thiourea compound is a compound represented by the following general formula (1):

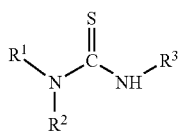

(1)

in the formula (1), $R^1$, $R^2$, and $R^3$ each represent a hydrogen atom, a hydroxyl group, a substituted or unsubstituted alkyl group, a substituted or unsubstituted cycloalkyl group, a substituted or unsubstituted aryl group, a substituted or unsubstituted heterocyclic group, a substituted or unsubstituted acyl group, a substituted or unsubstituted aralkyl group, or a substituted or unsubstituted alkenyl group, and $R^2$ may be bonded to any group selected from $R^1$ and $R^3$ to form a ring.

3. The chemical polymerization initiator according to claim 1, wherein (b) the peroxyester is a peroxyester having a 10-hour half-life temperature of 80° C. or more.

4. The chemical polymerization initiator according to claim 1,
wherein (c) the divalent copper compound contains a divalent copper atom and a ligand coordinating to the divalent copper atom,
wherein the ligand is selected from the group consisting of a halogen atom, an atomic group containing an oxygen atom, and an atomic group containing a nitrogen atom,
wherein when the ligand is the atomic group containing the oxygen atom, the atomic group containing the oxygen atom coordinates to the divalent copper atom through the oxygen atom, and
wherein when the ligand is the atomic group containing the nitrogen atom, the atomic group containing the nitrogen atom coordinates to the divalent copper atom through the nitrogen atom.

5. An adhesive composition, comprising:
(a) a thiourea compound;
(b) a peroxyester;
(c) a divalent copper compound;
(d) an aryl borate compound; and
(e) an acidic group-containing polymerizable monomer.

6. The adhesive composition according to claim 5, further comprising (f) an acidic group-free polymerizable monomer.

7. An adhesive composition kit, comprising a combination of a first partial composition and a second partial composition in a state of being incapable of physical contact with the first partial composition,
wherein an entirety of the combination of the first partial composition and the second partial composition contains at least five components formed of (a) a thiourea compound, (b) a peroxyester, (c) a divalent copper compound, (d) an aryl borate compound, and (e) an acidic group-containing polymerizable monomer,
wherein the first partial composition contains, as main components, (a) the thiourea compound and (d) the aryl borate compound out of the five components, and is substantially free of an organic peroxide, and
wherein the second partial composition contains, as main components, (b) the peroxyester, (c) the divalent copper compound, and (e) the acidic group-containing polymerizable monomer out of the five components, and is substantially free of a hydroperoxide.

8. The adhesive composition kit according to claim 7, wherein at least one composition selected from the first partial composition and the second partial composition further contains (f) an acidic group-free polymerizable monomer.

9. The adhesive composition kit according to claim 7, wherein at least one composition selected from the first partial composition and the second partial composition further contains at least one component selected from the group consisting of (g) a filler and (h) a solvent.

10. The adhesive composition kit according to claim 7,
wherein the first partial composition is formed only of (a) the thiourea compound, (d) the aryl borate compound, (f) an acidic group-free polymerizable monomer, and (g) a filler,
wherein the second partial composition is formed only of (b) the peroxyester, (c) the divalent copper compound, (e) the acidic group-containing polymerizable monomer, (f) an acidic group-free polymerizable monomer, and (g) a filler,
wherein (a) the thiourea compound is formed only of acetylthiourea,
wherein (b) the peroxyester is formed only of t-butyl peroxy-3,5,5-trimethylhexanoate,
wherein (c) the divalent copper compound is formed only of copper(II) acetate monohydrate, and
wherein (d) the aryl borate compound is formed only of a sodium salt of tetraphenylboric acid.

11. The adhesive composition kit according to claim 7,
wherein the first partial composition is formed only of (a) the thiourea compound, (d) the aryl borate compound, (f) an acidic group-free polymerizable monomer, and (g) a filler,
wherein the second partial composition is formed only of (b) the peroxyester, (c) the divalent copper compound, (e) the acidic group-containing polymerizable monomer, (f) an acidic group-free polymerizable monomer, and (g) a filler,
wherein (a) the thiourea compound is formed only of benzoylthiourea, wherein (b) the peroxyester is formed only of t-butyl peroxy-3,5,5-trimethylhexanoate, wherein (c) the divalent copper compound is formed only of copper(II) acetate monohydrate, and wherein (d) the aryl borate compound is formed only of a sodium salt of tetraphenylboric acid.

12. A dental material, comprising the adhesive composition of claim 5.

13. A dental material kit, comprising the adhesive composition kit of claim 7.

14. A method of storing an adhesive composition, comprising storing the adhesive composition of claim 5 under a state in which the adhesive composition is packaged into a first partial composition and a second partial composition, wherein the first partial composition contains, as main components, (a) the thiourea compound and (d) the aryl borate compound out of five components formed of (a) the thiourea compound, (b) the peroxyester, (c) the divalent copper compound, (d) the aryl borate compound, and (e) the acidic group-containing polymerizable monomer, and is substantially free of an organic peroxide, and wherein the second partial composition contains, as main components, (b) the peroxyester, (c) the divalent copper compound, and (e) the acidic group-containing polymerizable monomer out of the five components, and is substantially free of a hydroperoxide.

* * * * *